(12) United States Patent
Shorr et al.

(10) Patent No.: US 6,242,482 B1
(45) Date of Patent: Jun. 5, 2001

(54) PROSTAGLANDIN COMPOUNDS AND DERIVATIVES THEREOF, COMPOSITIONS CONTAINING THE SAME AND METHOD OF USING THE SAME FOR THE TREATMENT OF CONGESTIVE HEART FAILURE

(75) Inventors: Robert Shorr, Edison, NJ (US); Martine Rothblatt, Silver Spring, MD (US); Michael D. Bentley; Xuan Zhao, both of Huntsville, AL (US)

(73) Assignee: United Therapeutics Corporation, Silver Spring, MD (US)

( * ) Notice: Subject to any disclaimer, the term of this patent is extended or adjusted under 35 U.S.C. 154(b) by 0 days.

(21) Appl. No.: 09/587,458

(22) Filed: Jun. 5, 2000

(51) Int. Cl.[7] .................. A61K 31/34; A61K 31/215; A61K 31/165
(52) U.S. Cl. ..................... 514/469; 514/530; 514/621
(58) Field of Search .................... 514/469, 530, 514/621

(56) References Cited

FOREIGN PATENT DOCUMENTS

PCT/US00/
08240    8/2000  (WO) .

OTHER PUBLICATIONS

Hoper, Marius M. Et al., Tongji Medical University, "Prostanglandins induce vascular endothelial growth factor in a human monocytic cell line and rat lungs via cAMP", p. 40.

Tuder, Rubin M., American Lung Association, "Prostaglandins have emerged as a therapeutic option for patients with peripheral vascular disease", p. 41.

Shapiro, Shelley M. et al., J. Am. Coll. Cardiol. (1997), "Primary pulmonary hypertension: improved long–term effects and survival with continuous intravenous epoprostenol infusion", p. 43.

*Primary Examiner*—Raymond Henley, III
(74) *Attorney, Agent, or Firm*—Watov & Kipnes, P.C.

(57) ABSTRACT

Prostaglandin and analogs thereof which include protective groups attached to at least one site which are pharmaceutically acceptable and which are capable of slowing the metabolic rate of the active groups for administration to a warm blooded animal for the treatment of congestive heart failure.

51 Claims, 5 Drawing Sheets

EFFECT OF AEROSOLIZED 20kPEG-UT15 (ESTER) ON
U44069-INDUCED PULMONARY VASCULAR HYPERTENSION IN 1 SHEEP

FIG. 3

PROSTAGLANDIN COMPOUNDS AND DERIVATIVES THEREOF, COMPOSITIONS CONTAINING THE SAME AND METHOD OF USING THE SAME FOR THE TREATMENT OF CONGESTIVE HEART FAILURE

FIELD OF THE INVENTION

The present invention relates to modified prostaglandins, specifically long-acting prostaglandin-containing compositions for use in the treatment of congestive heart failure.

BACKGROUND OF THE INVENTION

Nearly every tissue in the body produces prostaglandins. No other autocoids or hormones show more numerous or diverse effects than prostaglandins. Due to rapid degradation which is most commonly caused by enzymes in the blood and lungs, the effective life of most prostaglandins is only about 3 to 10 minutes.

Prostaglandins including prostacyclin, a prostaglandin analog produced by the body and is implicated in maintaining proper function of blood vessels. Natural prostacyclin is inherently unstable, with an effective life of less than about six minutes. Prostaglandins including prostacyclins appear to act in three ways to keep blood vessels functioning properly, 1) they dilate blood vessels, where necessary, enabling proper blood flow ; 2) they prevent platelet aggregation thereby reducing its obstructive effects on blood vessels; and 3.) it contributes to regulation of proliferation of smooth muscle cells surrounding the vessels, which otherwise would constrict the vessels and further obstruct blood flow. These physiological effects of prostaglandins have been shown to provide therapeutic benefits in the treatment of congestive heart failure.

Congestive heart failure, regardless of its etiology, is characterized by a weakness of the myocardial tissue of the left and/or right ventricles of the heart and the resulting difficulty in pumping and circulating blood to the systemic and/or pulmonary systems. Myocardial tissue weakness is typically associated with circulatory and neurohumoral changes which result in a failure to deliver sufficient blood and oxygen to peripheral tissues and organs. Some of the resulting changes include higher pulmonary and systemic pressure, lower cardiac output, higher vascular resistance and peripheral and pulmonary edema. Congestive heart failure may be further expressed as shortness of breath either on exertion, at rest or paroxysmal nocturnal dyspnea. If left untreated, congestive heart failure can lead to death.

Prostaglandins have been shown to be useful for treating congestive heart failure in humans because of the positive effects generated by such compounds on blood flow through the prevention and reduction of undesirable constriction in blood vessels through vasodilation and anti-platelet effects on the blood. See, for example, Olschewski et al.: Inhaled iloprost to treat severe pulmonary hypertension, *Ann. Intem. Med.* 132:435–43 (2000); Sueta et al.: Safety and efficacy of epoprostenol in patients with severe congestive heart failure, *Am. J. Cardiol.* 75:34A-43A (1995); Kerins et al.: Prostacyclin and prostaglandin El: molecular mechanisms and therapeutic utility, *Prog. Hemost. Thromb.* 10:307–37 (1991); Montalescot et al.: Prostacyclin (epoprostenol) has a positive inotropic effect in patients with severe heart failure, *European Heart Journal* 18:292 (1997); Pacher et al.: Prostaglandin E1 infusion compared with prostacyclin infusion in patients with refractory heart failure: effects on hemodynamics and neurohumoral variables, *J. Heart Lung Transplant* 16:878–81 (1997); Patterson et al.: Acute hemodynamic effects of the prostacyclin analog 15AU81 in severe congestive heart failure, *Am. J. Cardiol.* 75: 26A-33A (1995); and Prostacyclin: basic principles and clinical application in congestive heart failure and primary pulmonary hypertension. Proceedings of a symposium. Bolgna, Italy, November20, 1993. Am. J. Cardiol. 75:1A-73A (1995). However, many prostaglandin and analogs thereof including prostacyclin, have very short effective lives, and provide relief for a short duration, before re-administration is required. Accordingly, any treatment using such prostaglandins would require continuous and sustained administration to provide effective therapy for the patient. It has been suggested that the short effective life of prostaglandins can actually place a stress on the heart by the rapid change in the vessels to facilitate blood flow. To date, the use of prostaglandins and analogs thereof has been severely limited in the treatment of congestive heart failure because of chemical instability, short effective life and limited effective modes of administration.

The short effective life of prostaglandins is due to a) rapid deactivation of the active groups of the molecules by enzymes, and b) their low molecular weight which makes them easily cleared or excreted from the body.

Prostaglandins have active sites typically in the form of hydroxyl and carboxyl groups. Enzymes can rapidly deactivate the active groups thereby rendering the compound ineffective. To overcome the problem, continuous infusion or frequent administration of high doses of prostaglandins have been employed to maintain therapeutically effective levels of the compound in the patient. Such dosage regimens, however, are disadvantageous because the treatment is expensive and there is a relatively high possibility of unwanted side effects including a possible increase in stress on the heart. Some of the side effects include nausea, swelling, gastrointestinal upset, jaw pain, rash, and headaches. In some patients severe adverse reactions have required discontinuing of treatment.

Numerous prostaglandins and analogs thereof such as prostacyclin have been prepared with the goal of discovering pharmaceutically acceptable agents that offer increased stability, a greater range of modes of administration, more effective activity and/or longer effective life. Investigators have sought prostaglandins and analogs thereof which can be effectively delivered orally to provide a less invasive and more convenient medical treatment. Current oral forms of prostaglandins and analogs thereof typically have an effective life of only up to about 1.5 hours and in some cases only a few minutes. The short effective life requires the patient to undertake frequent dosing, and therefore makes administration problematical for the patient, especially those suffering from chronic disease.

Conjugating biologically-active substances such as proteins, enzymes and the like to polymers has been suggested to increase the effective life, water solubility or antigenicity of the active substance in vivo. For example, coupling peptides or polypeptides to polyethylene glycol (PEG) and similar water-soluble polyalkylene oxides (PAO) is disclosed in U.S. Pat. No. 4,179,337, the disclosure of which is incorporated herein by reference. See also, Nucci M., Shorr R G L, and Abuchowski A., "Advanced Drug Delivery Reviews", 6:133–151: 1991; Harris J M (ed.); and "Polyethylene Glycol Chemistry: Biotechnical and Biomedical Application", Plenum Press, NY, 1992. Conjugates are generally formed by reacting a therapeutic agent with, for example, a several fold molar excess of a polymer which has been modified to contain a terminal linking group. The linking group enables the active substance to bind to the polymer. Polypeptides modified in this manner exhibit reduced immunogenicity/antigenicity and tend to have a higher effective life in the bloodstream than unmodified versions thereof.

To conjugate polyalkylene oxides with an active substance, at least one of the terminal hydroxyl groups is converted into a reactive functional group. This process is frequently referred to as "activation" and the product is called an "activated polyalkylene oxide." Other substantially non-antigenic polymers are similarly "activated" or "functionalized."

The activated polymers are reacted with a therapeutic agent having nucleophilic functional groups that serve as attachment sites. One nucleophilic functional group commonly used as an attachment site is the ε-amino groups of lysines. Free carboxylic groups, suitably activated carbonyl groups, oxidized carbohydrate moieties and mercapto groups have also been used as attachment sites.

Biologically active polymer conjugates can be formed having hydrolyzable bonds (linkages) between the polymer and the parent biologically-active moiety to produce prodrugs (where the parent molecule is eventually liberated in vivo). Several methods of preparing prodrugs have also been suggested. Prodrugs include chemical derivatives of a biologically-active parent compound which, upon administration, will eventually liberate the active parent compound in vivo. Prodrugs are advantageous because they enable modification of the onset and/or duration of action of a biologically-active compound in vivo. Prodrugs are often biologically inert or substantially inactive forms of the active compound. The rate of release of the active drug is influenced by several factors including the rate of hydrolysis of the linker which joins the biologically active compound to the prodrug carrier (e.g polymer).

Although prostaglandins and analogs thereof such as prostacyclin hold much promise as therapeutic agents, there is a need to a) improve the stability of such compounds, b) extend the effective life of the compounds to provide a more effective continuous level of the therapeutic agent in the patient to thereby minimize stress on the heart and c) enable the compounds to be administered in a more patient friendly dosage regimen than is currently available.

It would therefore be a significant advance in the art of drug therapy, especially for the treatment of congestive heart failure, if prostaglandins and analogs thereof and compositions employing the same can be developed which have improved stability, an effective life of sufficient duration to enable administration at a reasonable frequency, with less risk of heart stress from rapid changes in the levels of the therapeutic agents and in a more patient-friendly manner than current therapies employing prostaglandins and analogs thereof.

SUMMARY OF THE INVENTION

The present invention is generally directed to novel prostaglandin compounds and analogs thereof which possess activity suitable for the treatment of congestive heart failure including vasodilation of the associated blood vessels and anti-platelet effects on the blood.

The present invention provides compounds, compositions and methods of administering the compounds and compositions for the treatment of congestive heart failure. The compounds of the present invention have increased chemical stability and effective life, in a warm-blooded animal which improves delivery of the compound for treatment of congestive heart failure in the form of a pharmaceutically acceptable composition. Improved stability, effective life and more acceptable modes of administration and dosage regimens are achieved by modifying one or more of the active sites of the known prostaglandin compounds.

Thus, in one aspect of the present invention one or more active sites of the prostaglandin compounds or analogs thereof of the present invention are provided with a pharmaceutically acceptable group which slows the metabolic rate of the compound. A reduction in the metabolic rate provides an increase in the effective life of the active compound which a) provides a more efficient administration of the active compound, and b) enables a more patient-friendly dosage regimen.

In another aspect of the present invention, there is provided a method of treating a warm-blooded animal exhibiting congestive heart failure disease comprising administering to the animal a therapeutically effective amount of the modified prostaglandin compounds and analogs thereof of the present invention.

In another aspect of the present invention there is provided a compound having the Formula Ia or Ib as shown below

　　　　　　　　　　　　Ia

　　　　　　　　　　　　Ib wherein P is a prostaglandin compound or analog thereof, T represents a modified active group of P, Z is a pharmaceutically acceptable group which is bound to T and which slows the metabolic rate of said compound; and n is an integer of at least 1;

and pharmaceutically acceptable salts thereof.

BRIEF DESCRIPTION OF THE DRAWINGS

FIG. 3 is a graph depicting the effects of a dose of mPEG20 kDa-ester-Compound X, given as an aerosol, on the pulmonary arterial pressure of a sheep intravenously-induced with a pulmonary hypertensive agent;

DETAILED DESCRIPTION OF THE INVENTION

Figure 1:
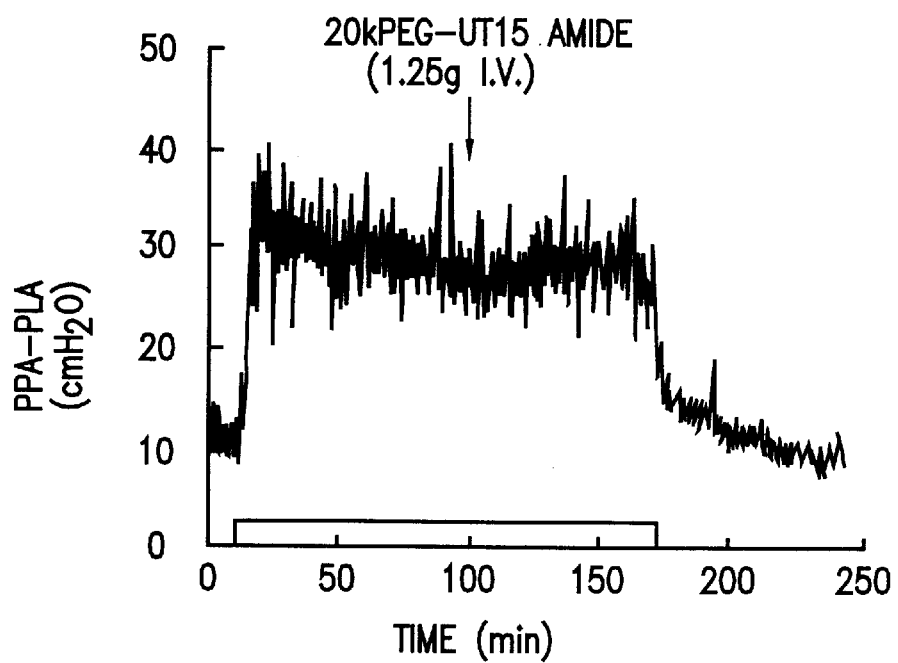
FIG. 1 is a graph showing the effects on pulmonary arterial pressure of a dose of mPEG20 kDa-amide-Compound X, given as an intravenous infusion to a sheep intravenously-induced with a pulmonary hypertensive agent.

The present invention is directed to novel prostaglandins and analogs thereof in which at least one active site has attached thereto an inert, non-antigenic, non-immunogenic group having a structure which protects the active site when administered to a warm-blooded animal including humans and therefore provides a longer effective life for the compound. As a result more of the compound is available for treating congestive heart failure by being present to treat the major blood vessels which service the heart for a longer period of time. Because more of the active compound is available, dosage regimens may be less burdensome to the patient. As used herein the term "effective life" shall mean the time period during which the present compounds are in their active form in a warm-blooded animal.

The protection of at least one active group generally increases the effective life of the prostaglandin compounds and therefore makes them more suitable for various modes of administration and provides less risk of heart stress which may result from rapid changes in the level of the therapeutic agents as compared to native or unprotected forms of the prostaglandin compounds.

As used herein the term "prostaglandin compounds and analogs thereof", hereinafter collectively referred to as "prostaglandin compounds", shall mean all prostaglandin compounds, and variations thereof which have at least one active group, (e.g., a COOH group and/or an OH group) and which are at least minimally effective for the treatment of congestive heart failure in warm-blooded animals. As used herein, the term "present prostaglandin compounds" shall refer to prostaglandin compounds as defined, which have been modified in accordance with the present invention. As used herein, the term "active group" shall mean a site on the prostaglandin compound, which is capable of binding to or otherwise engaging a targeted tissue such as vascular tissue.

The present invention includes present prostaglandin (PG) compounds of all types. For example, the present prostaglandin compounds employed in the present invention include modified PGA, PGB, PGC, PGD, PGE, PGF, and PGI type compounds as well as all subtypes of the foregoing with PGE being preferred. The prostaglandin compounds can be isolated or extracted from a warm-blooded animal source or prepared synthetically by techniques known to those of ordinary skill in the art.

Preferred present prostaglandin compounds are represented by Formula II

Formula II wherein
$Z_1$ and $Z_2$ are independently selected from hydrogen and the groups previously defined for Z in Formula I, with the proviso that at least one of $Z_1$ and $Z_2$ is not hydrogen; and
X is selected from O or NH.

More highly preferred compounds of Formula II are compounds of Groups 1, 2 and 3 as defined below, wherein:
for the Group 1 compounds:

$Z_1$ is a pharmaceutically acceptable polymer which binds to X and slows the metabolic rate of the compound; and
X is selected from O and NH, and $Z_2$ is selected from H and an acetyl group; for the Group 2 compounds:
$Z_1$ is hydrogen;
X is O, and $Z_2$ is a pharmaceutically acceptable polymer which slows the metabolic rate of the compound and is attached to the oxygen through an ester group; and
for the Group 3 compounds:
$Z_1$ is a pharmaceutically acceptable polymer as defined in Group 1;
X is O or NH, and $Z_2$ is a pharmaceutically acceptable polymer as defined in Group 2, attached to the oxygen through an ester group.

Preferred compounds are also represented by Formula III

Formula III wherein
$Z_1$ and $Z_2$ include the same groups as previously defined in Formula II;
f is an integer of from 1 to 3;
X is selected from O and NH; and
R is selected from hydrogen and an alkyl group preferably having 1–6 carbon atoms.

More highly preferred compounds of Formula III are compounds of Groups 4, 5 and 6, wherein:
for the Group 4 compounds:
$Z_1$ is a pharmaceutically acceptable polymer which binds to X and slows the metabolic rate of the compound;
X is selected from O and NH, and $Z_2$ is selected from hydrogen and an acetyl group;
for the Group 5 compounds:
$Z_1$ is hydrogen, X is O, and $Z_2$ is an acetyl group, or a pharmaceutically acceptable polymer which slows the metabolic rate of the compound and is attached to the oxygen through an ester or ether group;
for the Group 6 compounds:
$Z_1$ is a pharmaceutically acceptable polymer as defined in Group 4, X is selected from O and NH, and $Z_2$ is a pharmaceutically acceptable polymer as defined in Group 5.

Highly preferred compounds are those where the $Z_1$ and/or $Z_2$ groups are polyethylene glycols having the formula $CH_3OCH_2CH_2(OCH_2CH_2)_a$, wherein a is from 1 to about 1000.

A particularly preferred group of present prostaglandin compounds are those having the Formula IV Formula IV

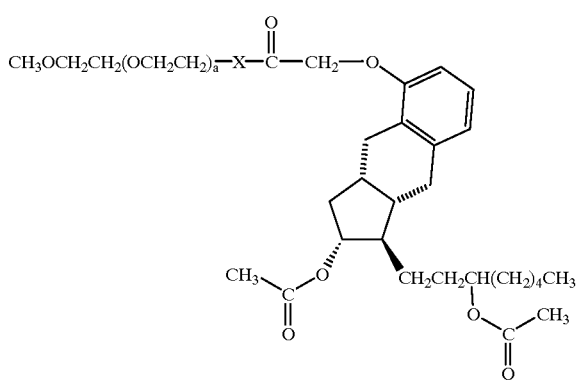

wherein a and X are as defined above. Preferably a is from about 6 to 600, most preferably from about 6 to 460.

The present invention also provides a method of treating a warm-blooded animal afflicted with congestive heart failure comprising administering to the warm-blooded animal an effective amount of a compound of Formula I. Compositions containing such compounds which are suitable for administration to warm-blooded animals for the purposes are part of the present invention.

Congestive heart failure is characterized by abnormal constriction of blood vessels causing decrease in blood flow and increase in vascular resistance to the detriment of the heart. Administration of present prostaglandin compounds to a patient afflicted with congestive heart failure, promotes increased blood flow through the afflicted blood vessels by reducing vascular resistance through easing of blood vessel constriction. As a result less strain is placed on the heart and higher levels of oxygen are available for heart tissue. Furthermore, anti-platelet aggregatory and cytoprotective activities of the present prostaglandin compounds is believed to promote healing by inhibiting inflammatory response in damaged tissue and minimize obstructions that would otherwise increase vascular resistance.

It is believed that vasodilation is triggered by the present prostaglandin compounds and results in the relaxation of smooth muscle in the peripheral arterial vessels of the heart. In combination, these effects induce a substantial drop in systemic and pulmonary arterial pressure and vascular resistance, and an increase in cardiac output. In patients with congestive heart failure, these responses would enable the heart to pump more blood and relieve the symptoms associated with poor ventricular performance.

In one aspect of the present invention, one or more of the active groups of the present prostaglandin compounds (e.g., COOH and OH) are attached to linear, branched and/or circular polymers and copolymers which are inert, non-antigenic and non-immunogenic. In addition, the polymers must be capable of separating from the present prostaglandin compounds at a rate which is suitable for delivering the present prostaglandin compounds to the systemic and pulmonary blood vasculature of the warm-blooded animal. To the extent that any of the polymer remains attached to the prostaglandin compound, it should not adversely affect the treatment of congestive heart failure.

To conjugate prostaglandin compounds to polymers such as polyalkylene oxides, one or more of the hydroxyl groups of the polymer is converted into a reactive functional group which allows conjugation.

The activated polymers are reacted with the prostaglandin compound so that attachment preferably occurs at the free carboxylic acid groups and/or hydroxyl groups. Suitably activated carbonyl groups, oxidized carbohydrate moieties and mercapto groups if available or made available on the prostaglandin compound can also be used as conjugation sites.

In a preferred aspect of the invention, amide or ester linkages are formed between the carboxylic or hydroxyl groups and the activated polyalkylene oxides. Polymers activated with urethane-forming linkers or the like, and other functional groups which facilitate attachment of the polymer to the prostaglandin compound via carboxylic or other groups are encompassed by the present invention.

Among the substantially non-antigenic polymers, polyalkylene oxides (PAO's) especially mono-activated, alkyl-terminated polyalkylene oxides such as polyethylene glycols (PEG) and especially monomethyl-terminated polyethylene glycols (mPEG's). Bis-activated polyethylene oxides are also contemplated for purposes of cross-linking the prostaglandin compound or providing a means for attaching other moieties such as targeting agents for localizing the polymer-prostaglandin conjugate in the target area such as, for example, the lungs or blood vessels in the extremities.

Suitable polymers especially PEG or mPEG, will vary substantially by weight. Polymers having molecular weights ranging from about 200 to about 80,000 daltons are typically employed in the present invention. Molecular weights from about 2,000 to 42,000 daltons are preferred, and molecular weights of from about 5,000 to 28,000 daltons are particularly preferred.

The polymers preferably employed in the present invention as protective groups are water-soluble at room temperature. A non-limiting list of such polymers include polyalkylene oxide homopolymers such as PEG and mPEG or polypropylene glycols, polyoxyethylenated polyols, copolymers thereof and block copolymers thereof. In addition to mPEG, $C_{1-4}$ alkyl-terminated polymers are also useful.

As an alternative to PAO-based polymers, effectively non-antigenic materials such as dextran, polyvinyl pyrrolidones, polyacrylamides, polyvinyl alcohols, carbohydrate-based polymers and the like can be used. Modifications of the prostaglandin compounds may further include, but are not limited to, acetylation, carboxylation, glycosylation, phosphorylation, lipidation, and acylation. Those of ordinary skill in the art will realize that the foregoing list is merely illustrative and that all polymer materials having the qualities herein are contemplated.

The prostaglandin compounds are coupled to the protective groups as described to provide present prostaglandin compounds which effectively deliver the active compound to the target area and maintain the present prostaglandin compound within the target area for a longer period of time than achieved with known prostaglandin compounds. The present prostaglandin compounds are therefore particularly suited for the treatment of congestive heart failure.

As previously indicated, many of the known prostaglandin compounds which are used in congestive heart failure therapy have a very short effective life in a warm blooded animal, typically less than one hour. In accordance with the present invention, present prostaglandin compounds are provided which have an improved effective life which may last up to several hours. A longer effective life reduces the number of potentially damaging dramatic changes in levels of the therapeutic agent as well as reduce the number of times that the present prostaglandin compound may be administered. The present prostaglandin compounds may therefore be delivered in lower dosage unit amounts and with less frequency and less risk to the patient.

The active groups of the present prostaglandin compounds include COOH and OH groups. One or more of these active groups are protected by a protective group as more specifically set forth hereinafter. The protective groups may generally have a molecular weight of up to 500,000 or more. In a preferred form of the invention, a group having a molecular weight of at least 5,000 daltons should be conjugated to the COOH when the OH groups are not protected, more preferably at least 20,000 daltons. It has also been observed that protective groups of molecular weight of at least 5,000 daltons can slow excretion of the compounds, thereby contributing to increased effective life in a warm blooded animal.

The protective groups are any groups which serve to protect the active groups (COOH and OH) from premature metabolism but can readily separate from the active groups in a controlled manner and/or may be attached to the active group without adversely affecting the function of the compound. Such protective groups include, for example, polymers, straight and branched chain alkyl groups, aralkyl groups, aryl groups, acyl groups, heterocyclic groups, alkylene groups all of which may be substituted with substituents selected from, for example, alkyl, aryl, and aralkyl groups and the like.

Among the polymers that may be conjugated to the active group include polyglycols, polyvinyl polymers, polyesters, polyamides, polysaccharides, and polymeric acids, lipids, amino acids, nucleic acids, carbohydrates, and combinations thereof.

The preferred polyglycols include polyethylene glycol and polypropylene glycol.

The preferred polysaccharides are those selected from polysaccharide B.

Among the polyacids which may preferably be used in accordance with the present invention, are polyamino acids and polyactic acid.

The preferred polymers among the classes of polymers mentioned above are polyethylene glycols (PEG).

In addition to the polymers mentioned above, such polymers as dextran, cellulosic polymers and starches may be also used in accordance with the present invention.

The polymers may be attached to the active COOH or OH group through a group such as for example, an amide group, an ester group or the like.

The compounds of Formula I are typically employed as part of a pharmaceutical composition including a pharmaceutically acceptable carrier for the treatment of cardiovascular disease including congestive heart failure. The compounds employed for this purpose are typically administered in an amount of from 0.5 to 100 mg/kg/day, preferably from about 25 to 35 mg/kg/day.

The pharmaceutical composition comprising at least one compound of Formula I may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those known in the art of pharmaceutical formulation.

The compounds of Formula I may be administered by any suitable means, for example, orally, such as in the form of tablets, capsules, granules or powders; sublingually; bucally; parenterally, such as subcutaneous, intravenous, intramuscular, or intrasternal injection or infusion techniques (e.g., as sterile injectable aqueous or non-aqueous solution or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present prostaglandin compounds may be based for immediate release or extended release by the use of suitable pharmaceutical compositions comprising the present compounds, or, particularly in the case of extended release, by the use of devices such as subcutaneous implants or osmotic pumps. The present invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose, and/or cyclodextrins. Also included in such formulations may be high molecular weight excipients such as celluloses (avicel). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g. Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter or synthetic glyceride esters, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of the present prostaglandin compound may be determined by one of ordinary skill in the art, and includes exemplary dosage amounts for an adult human from about 0.5 to 100 mg/kg of body weight of present prostaglandin compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to heart failure.

Generally, a significantly lower dosage of the present prostaglandin compounds, in comparison with known native or unconjugated prostaglandin compounds, is required to obtain the desired effect, i.e. vasodilating the associated diseased vasculature. Because of the rapid metabolism of native or unconjugated forms of known prostaglandin compounds in vivo and the resulting rapid changes in the levels of therapeutic activity which may contribute to stress of the heart, long continuous infusions of relatively large doses of these drugs have been required to maintain an effective blood level in the patient being treated. However, hypotension, tachycardia, and diarrhea, among other side effects, caused by high blood levels of known prostaglandin compounds limit the amount of the known prostaglandin compounds which can be administered. The high cost of prostaglandin compounds makes it prohibitively expensive to administer such large doses to the patient. The methods of the present invention provide for effective administration of the present prostaglandin compounds, at reduced cost and with reduced side effects.

The present prostaglandin compounds of the present invention may be administered subcutaneously in the form of a liquid reconstituted form a lyophilized powder which may additionally contain preservatives, buffers, dispersants, etc. Preferably, the prostaglandin compounds are reconstituted with a medium normally utilized for intravenous injection, e.g., preservative-free sterile water. Administration may be accomplished by continuous intravenous or subcutaneous infusion or by intravenous injection. For continuous infusion, the daily dose can be added to normal saline or other solution and the solution infused by mechanical pump or by gravity.

The following examples illustrate embodiments of the present invention. One skilled in the art will readily recognize that changes, modifications and variations can be made therein without departing from the spirit and scope of the invention as defined in the claims forming part of the application.

EXAMPLE 1

Synthesis of mPEG-5kDa-amide-Compound X hereinafter referred to as "Compound 1"

A compound of Group 4 wherein $Z_1$ is a mPEG with a molecular weight of about 5,000 daltons, X is NH and $Z_2$ is hydrogen was prepared in the following manner.

200 mg of Compound X having the formula shown below:

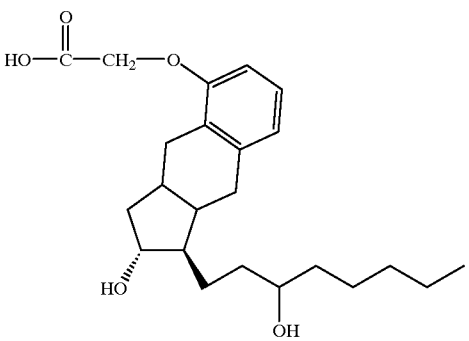

Compound X was placed in a round bottom flask along with mPEG5 k amine (2.5 g), 2-hydoxybenzyltriazole (HOBT, 67 mg), 4-(dimethylamino)pyridine (DMAP, 61 mg) and dicyclohexylcarbodiimide (DCC, 140 mg). The materials were mixed with 60 ml of anhydrous methylene chloride. The mixture was stirred at room temperature overnight and thereafter the solvent was removed by vaporization. The residue was dissolved in 25 ml of 1,4 dioxane and the insoluble solid was removed by filtration. The solvent was condensed and then precipitated into 100 ml of 50:50/ ether:isopropanol. The precipitate was collected by filtration and dried under vacuum. The resulting yield was 2.5 g (93%). $^1$H NMR(DMSO-$d_6$): δ3.5 (br m, PEG), 7.897 (t, -PEGN$\underline{H}$-CO-(Compound X)), 4.49 (d, (Compound X)-O $\underline{H}^1$), 4.24 (d, (Compound X)-O$\underline{H}^2$), 0.864 (t, (Compound X)-C$\underline{H}_3$), 4.436 (s, (Compound X)-C$\underline{H}_2$CONHPEG), 7.045 (t, Compound X aromatic proton), 6.7 (d+d, Compound X aromatic proton).

EXAMPLE 2

Synthesis of mPEG5 kDa-ester-Compound X diacetate hereinafter referred to as "Compound 2"

A compound of Group 4 wherein $Z_1$ is a mPEG with a molecular weight of about 5,000 daltons, X is O and each $Z_2$ is an acetyl group, was prepared in the following manner.

In a round-bottom flask, Compound X (400 mg) and pyridine (200 μl) were mixed in 35 ml of anhydrous methylene chloride. 500 μl of acetic anhydride was added to the suspension. The mixture became homogenous in a few hours and the solution was stirred at room temperature overnight. The solvent was condensed and phosphate buffer (0.1 M, pH 7.4) was added to the residue. The mixture was rapidly stirred for 30 minutes, and the mixture was extracted with methylene chloride three times. The combined organic phase was dried over sodium sulfate, and the solvent was removed by vaporization. An oily product, Compound X diacetate, was obtained. The yield was 340 mg (80%). $^1$H NMR (DMSO-$d_6$): 1.91 (s, (Compound X)-O$^1$COC$\underline{H}_3$), 2.00 (s, (Compound X)-O$^2$COC$\underline{H}_3$), 0.84 (t, (Compound X)-CH$_3$).

In a round-bottom flask, mPEG5 k (3.8 g), Compound X diacetate from the previous step (320 mg), 2-hydroxybenzyltriazole (HOBT, 103 mg), 4-(dimethylamino)pyridine (DMAP, 93 mg) and dicyclohexylcarbodiimide (DCC, 238 mg) were dissolved with 50 ml of anhydrous methylene chloride. The solution was stirred at room temperature overnight and the solvent removed by vaporization. The residue was dissolved in 35 ml of 1,4 dioxane and the insoluble solid was removed by filtration. The solvent was condensed and then precipitated into 100 ml of 50:50/ether: isopropanol. The precipitate was collected by filtration and dried under vacuum. The resulting yield was 3.2 g (78%). $^1$H NMR(DMSO-$d_6$): δ3.5 (br m, PEG), 4.23 (t, -PEGOCH$_2$C$\underline{H}_2$O—CO-(Compound X)), 1.91 (s, (Compound X)-O$^1$COC$\underline{H}_3$), 2.00 (s, (Compound X)-O$^2$COC$\underline{H}_3$), 0.84 (t, (Compound X)-CH$_3$), 4.77 (s, (Compound X)-C$\underline{H}_2$COOPEG), 7.03 (t, Compound X aromatic proton), 6.7 (d+d, Compound X aromatic proton).

EXAMPLE 3

Synthesis of mPEG20 KDa-ester-Compound X hereinafter referred to as "Compound 3"

A compound of Group 5 wherein each $Z_2$ is a mPEG having a molecular weight of about 20,000 daltons attached through a group —CO—(CH$_2$)$_2$—O—, was prepared in the following manner.

In a round-bottom flask, Compound X (200 mg) and sodium hydroxide (21 mg) were mixed in 40 ml of anhydrous acetonitrile. 90 mg of benzyl bromide was added to the suspension and the mixture was refluxed for two days. The solid was removed by filtration, the solvent condensed, and the residue dried under vacuum. An oily product, Compound X-benzyl ester, was obtained. The yield was 210 mg (100%). $^1$H NMR(DMSO-$d_6$): δ7.37 (s, C$_6$$\underline{H}_5$—CH$_2$—OCO-(Compound X)), 5.19 (s, C$_6$H$_5$—C$\underline{H}_2$—OCO-(Compound X)), 4.83 (s, (Compound X)-C$\underline{H}_2$COOBz), 4.49 (d, (Compound X)-O$\underline{H}^1$), 4.24 (d, (Compound X)-O$\underline{H}^2$), 0.864 (t, (Compound X)-C$\underline{H}_3$), 7.025 (t, Compound X aromatic proton), 6.7 (d+d, Compound X aromatic proton).

In a round-bottom flask, mPEG 20 k (3 g), Compound X-benzyl ester (prepared in the previous step, 100 mg), HOBT (3 mg), DMAP (25 mg) and DCC (42 mg) were dissolved in 40 ml of anhydrous methylene chloride. The solution was stirred at room temperature overnight, and the solvent was removed by vaporization. The residue was dissolved in 30 ml of 1,4 dioxane and the insoluble solid was removed by filtration. The solvent was condensed and then precipitated into 100 ml of 50:50/ether:isopropanol. The precipitate was collected by filtration and dried under vacuum. The yield was 2.7 g (90%). $^1$H NMR(DMSO-$d_6$): δ3.5 (br m, PEG), 2.48 (t, mPEG-OCH$_2$C$\underline{H}_2$COO-(Compound X)), 7.35 (s, C$_6$$\underline{H}_5$-CH$_2$—OCO-(Compound X)), 5.17 (s, C$_6$H$_5$—CH$_2$—OCO-(Compound X)), 4.83 (s, (Compound X)-C$\underline{H}_2$COOBz), 0.857 (t, (Compound X)-C$\underline{H}_3$), 7.025 (t, Compound X aromatic proton), 6.7 (d+d, Compound X aromatic proton).

A solution of mPEG- Compound X benzyl ester (obtained in the previous step, 2.7 g) in 1,4-dioxane (30 ml) was hydrogenated with H$_2$ (2 atm pressure) and 1 gram of Pd/C (10%) overnight. The catalyst was removed by filtration and the catalyst was washed with fresh methylene chloride. The combined solution was condensed by rotary evaporation and the residual syrup was added into 300 ml of ethyl ether. The product was collected by filtration and dried under vacuum. The yield was 2 gram (74%). $^1$H NMR(DMSO-$d_6$): δ3.5 (br m, PEG), 2.48 (t, mPEG-OCH$_2$C$\underline{H}_2$COO-(Compound X)), 4.61 (s, mPEG-(Compound X)-C$\underline{H}_2$COOH), 0.857 (t, (Compound X)-C$\underline{H}_3$), 7.025 (t, Compound X aromatic proton), 6.7 (d+d, Compound X aromatic proton).

EXAMPLE 4

Anti-Platelet Effects of Compound X and Compounds 1–3 on Human Plasma in Vitro

Introduction

The anti-platelet activity of Compound X and Compounds 1–3 of the present invention on human plasma taken from healthy human volunteers was determined in the following manner. In addition, the anti-platelet responses of each compound following incubation with platelet-poor plasma (PPP) and with aqueous vehicle (acetate buffer) for various times were measured. By observing the anti-aggregatory effects of the above compounds, the duration and magnitude of activity can be measured. It is believed that the anti-aggregatory effects are beneficial in the treatment of congestive heart failure by preventing or minimizing the aggregation of platelets in the blood vessels, thus maintaining a relatively unobstructed circulatory pathway.

Methods

Preparation of Platelet-Rich Plasma (PRP)

Blood from healthy human volunteers who had not taken any medicine for at least 14 days was collected by venopuncture into 3.15% (w/v) tri-sodium citrate (9:1 v/v). The blood was centrifuged at 800 g for 15 minutes to produce PRP. The PRP was further centrifuged at 12,000 g for 1 minute to produce PPP.

Photometric Measurement of Platelet Aggregation

Platelet aggregation was measured using a dual channel Payton aggregometer calibrated with PRP (0%) and PPP (100%) with respect to the degree of light transmission. Aliquots of PRP (500 µl) were added to siliconized cuvettes, stirred (1000 revs/min) and warmed to 37° C. The platelets were incubated for 1 minute to establish a stable baseline prior to testing. A submaximal concentration of the aggregating agent collagen (1 µg/ml) was added to the PRP and the platelet aggregation was monitored as the increase in light transmission observed over a 4 minute period.

Anti-Aggregatoty Response

Compound X (1–100 ng/ml) and Compounds 1–3 (0.1–10 mg/ml) were each incubated with PRP for 1 minute prior to the addition of collagen (1 µg/ml), a clotting agent. The percent inhibition of the platelet aggregation was calculated using the peak increase in light transmission observed over the 4 minute period following the addition of collagen, as compared to that of the control. This experiment was repeated using PRP from at least three human volunteers.

The test results are presented in Table 1. The results in Table 1, exemplify the concentration-dependent effects of Compound X and Compounds 1 through 3 on human platelet aggregation under the test conditions described above.

Anti-Aggregatory Response After Incubation with Aqueous Vehicle and PPP

In separate experiments, samples of Compound X (30 and 300 ng/ml) and samples of Compound 1 (0.3 and 3 mg/ml); Compound 2 (0.03, 0.3 and 3 mg/ml); and Compound 3 (3 mg/ml) were incubated with 500 µl of an aqueous vehicle (Acetate Buffer) for various times including 15 minutes, 1 hour, and 4 hours at 37° C. After the incubation period, a 50 µl aliquot of the aqueous vehicle with the corresponding sample compound was added to fresh PRP (450 µl) for determination of anti-aggregatory activity following challenge with collagen. This experiment was repeated using PPP from at least three human volunteers. The effects of Compound X and Compounds 1–3 on human platelet aggregation after incubation with an aqueous vehicle (acetate buffer) for 15 minutes, 1 hour and 4 hours are, respectively, detailed in Table 2. The effects of Compound X and Compounds 1–3 on human platelet aggregation after incubation with PPP for 15 minutes, 1 hour and 4 hours, respectively, are detailed in Table 3. The data in both Tables 2 and 3 are shown as the mean and the standard error of n number of donors.

Results

Effects of Compound X on Platelet Aggregation

As shown in Table 1, Compound X (1–100 ng/ml), incubated with PRP for 1 minute prior to the addition of collagen, caused a concentration-dependent inhibition of collagen-induced platelet aggregation. At the higher concentrations (30 and 100 ng/ml), Compound X completely inhibited the aggregation response (see Table 1). The concentration of Compound X inhibiting aggregation by 50% ($ID_{50}$) was determined to be 20 ng/ml.

Referring to Table 3, the incubation of Compound X (3 and 300 ng/ml) with PPP for 15 minutes, 1 hour and 4 hours, had no significant effect on the anti-platelet activity. Likewise, the incubation of Compound X (30 and 300 ng/ml) with the aqueous vehicle alone for 15 minutes, 1 hour and 4 hours had no significant effect on the degree of anti-platelet activity, as shown in Table 2.

Effects of Compound 1 on Platelet Aggregation

Compound 1 (0.1–3 mg/mi), incubated with PRP for 1 minute prior to the addition of collagen, caused a concentration-dependent inhibition of platelet aggregation, as shown in Table 1. At the highest concentration (3 mg/ml), Compound 1 completely inhibited the aggregation response to collagen (see Table 1). By comparison to the anti-aggregatory activity of Compound X, Compound 1 was about $10^5$ times less active in inhibiting platelet aggregation after 1 minute of incubation.

As shown in Table 3, the anti-aggregatory activity of Compound 1 was increased in a time-dependent manner following incubation with PPP for 1 hour and 4 hours, respectively. Thus, after 1 hour, the activity had increased by 7-fold, while after 4 hours, this activity was some 22-fold greater than the activity observed after 1 minute incubation (see Table 3).

By comparison, incubation of Compound 1 with aqueous vehicle alone had no effect on anti-platelet activity at any time point tested (see Table 2).

Effects of Compound 2 on Platelet Aggregation

As shown in Table 1, compound 2, at the highest concentration evaluated (10 mg/ml), cause approximately 20% inhibition of platelet aggregation when incubated with PRP for 1 minute. Lower concentrations of Compound 2 had no significant anti-platelet activity after this 1 minute incubation (see Table 1).

As shown in Table 3, the activity of Compound 2 was observed to substantially increase in a time-dependent manner following incubation with PPP for 1 hour and 4 hours. This activity had increased by 50-fold when incubated for 1 hour in PPP as compared to 1 minute of incubation. Furthermore, this activity was increased by at least 3,500-fold greater after 4 hour incubation than activity observed after 1 minute incubation (see Table 3).

However, incubation of Compound 2 with aqueous vehicle alone had no such effect on anti-platelet activity at any time point tested (see Table 2).

Effects of Compound 3 on Platelet Aggregation

As shown in Table 1, Compound 3 (0.3–10 mg/ml), incubated with PRP for 1 minute, caused a concentration-dependent inhibition of platelet aggregation. At the highest concentration (10 mg/ml), Compound 3 completely inhibited the aggregation response (see Table 1).

Incubation of Compound 3 (300 μg/ml) with PPP for 4 hours, at a concentration that was ineffective after 1 minute, caused an increase in activity, reaching 40% inhibition of platelet aggregation (see Table 3). Because of the weak activity even after this period of incubation, no further concentrations were evaluated.

Incubation of Compound 3 with aqueous vehicle had no effect on anti-platelet activity at any time point tested (see Table 2).

Conclusion

These present findings with the samples of Compound X and Compounds 1–3 indicate that inclusion of a PEG moiety of 5,000 to 20,000 Dalton molecular weight, along with acetate groupings, reduces anti-aggregatory activity of Compound X. However, the activity of these compounds increases during incubation over a four (4) hour period with human plasma, but not with buffer alone, indicating the presence of enzymatic hydrolysis of these derivatives which indicates prolonged release of the active compound. Such prolonged effect provides an effective and consistent response beneficial for maintaining improved blood flow by minimizing aggregation of blood platelets in the blood vessels.

TABLE 1

Concentration-dependent Effects of Compound X and Compounds 1–3 on Human Platelet Aggregation

| Compound Concentration (Final) | Platelet Aggregation (% of Control) | | | | | | | | | | | |
|---|---|---|---|---|---|---|---|---|---|---|---|---|
| | Compound X | | | Compound 1 | | | Compound 2 | | | Compound 3 | | |
| | Mean | SEM | n | Mean | SEM | n | Mean | SEM | n | Mean | SEM | n |
| 1 ng/ml | 101 | 1 | 3 | | | | | | | | | |
| 3 ng/ml | 98 | 1 | 3 | | | | | | | | | |
| 10 ng/ml | 60 | 24 | 3 | | | | | | | | | |
| 30 ng/ml | 1 | 1 | 3 | | | | | | | | | |
| 100 ng/ml | 1 | 1 | 3 | | | | | | | | | |
| 100 μg/ml | | | | 94 | 7 | 3 | | | | | | |
| 300 μg/ml | | | | 95 | 4 | 3 | | | | 100 | 1 | 3 |
| 1 mg/ml | | | | 90 | 7 | 3 | 100 | 3 | 3 | 98 | 2 | 3 |
| 3 mg/ml | | | | 1 | 1 | 3 | 95 | 2 | 3 | 80 | 8 | 3 |
| 10 mg/ml | | | | | | | 78 | 10 | 3 | 1 | 1 | 3 |

TABLE 2

Effects of Compound X and Compounds 1–3 on Human Platelet Aggregation after Incubation with Aqueous Vehicle (Acetate Buffer)

| Compound Concentration (Final) | Platelet Aggregation (% of Control) | | | | | | | | |
|---|---|---|---|---|---|---|---|---|---|
| | 15 Minutes | | | 1 Hour | | | 4 Hours | | |
| | Mean | SEM | n | Mean | SEM | n | Mean | SEM | n |
| Comp. X (3 ng/ml) | 98 | 2 | 3 | 107 | 2 | 3 | 94 | 3 | 3 |
| Comp. X (30 ng/ml) | 3 | 3 | 3 | 8 | 8 | 3 | 8 | 8 | 3 |
| Comp. 1 (30 µg/ml) | 102 | 3 | 3 | 105 | 4 | 3 | 98 | 3 | 4 |
| Comp. 1 (300 µg/ml) | 105 | 3 | 3 | 104 | 3 | 3 | 97 | 3 | 4 |
| Comp. 2 (3 µg/ml) | 105 | 1 | 4 | 107 | 3 | 4 | 99 | 2 | 4 |
| Comp. 2 (30 µg/ml) | 102 | 2 | 4 | 104 | 5 | 4 | 97 | 3 | 4 |
| Comp. 2 (300 µg/ml) | 103 | 3 | 3 | 104 | 4 | 3 | 98 | 2 | 3 |
| Comp. 3 (300 µg/ml) | 103 | 2 | 3 | 103 | 2 | 3 | 91 | 2 | 4 |

TABLE 3

Effects of Compound X and Compounds 1–3 on Human Platelet Aggregation after Incubation with Human PPP

| Compound Concentration (Final) | Platelet Aggregation (% of Control) | | | | | | | | |
|---|---|---|---|---|---|---|---|---|---|
| | 15 Minutes | | | 1 Hour | | | 4 Hours | | |
| | Mean | SEM | n | Mean | SEM | n | Mean | SEM | n |
| Comp. X (3 ng/ml) | 101 | 2 | 3 | 100 | 3 | 3 | 91 | 5 | 3 |
| Comp. X (30 ng/ml) | 1 | 1 | 3 | 1 | 1 | 3 | 1 | 1 | 3 |
| Comp. 1 (30 µg/ml) | 101 | 2 | 3 | 107 | 3 | 3 | 84 | 4 | 4 |
| Comp. 1 (300 µg/ml) | 95 | 5 | 3 | 45 | 23 | 3 | 1 | 1 | 4 |
| Comp. 2 (3 µg/ml) | 102 | 3 | 4 | 105 | 2 | 4 | 78 | 5 | 4 |
| Comp. 2 (30 µg/ml) | 99 | 3 | 4 | 102 | 2 | 4 | 1 | 1 | 4 |
| Comp. 2 (300 µg/ml) | 101 | 4 | 4 | 75 | 12 | 3 | 1 | 1 | 4 |
| Comp. 3 (300 µg/ml) | 97 | 7 | 3 | 101 | 2 | 3 | 69 | 6 | 4 |

EXAMPLE 5

Systemic Hemodynamic Effects of Intravenously Administered Compound X and Compounds 1–3 in Anesthetized Rats in Vivo Introduction This study reports on the potency, activation and duration of biological activity of Compounds 1–3 in comparison to Compound X in thiopentone-anesthetized rats. The effects of these compounds on blood pressure (BP) and heart rate following bolus intravenous injection were observed for each of the compounds. The time for onset and maximal response were evaluated, as well as the time taken for the response to return to 50% of the baseline value for comparing effective lives. Among other effects, lowering of the blood pressure inside the blood vessels is beneficial for the treatment of congestive heart failure by reducing the vascular resistance blood flow, and thus the work load imposed on the heart. As a result, the heart does not have to work as hard to pump blood through the vessels.

Materials and Methods

Male Wistar rats were anesthetized with thiopentone sodium (INTRAVAL®, 120 mg kg$^{-1}$ i.p.). The trachea was cannulated to facilitate breathing. The right carotid artery was cannulated and connected to a pressure transducer (Spectramed P23XL), for the measurement of mean arterial pressure (MAP) and heart rate (HR) which were continuously recorded on a 4-channel Grass 7D polygraph recorder (Grass, Mass., USA). The left femoral vein or the right jugular vein was cannulated for the administration of drugs. The body temperature of the test animal was maintained at 37±1° C. by means of a rectal probe thermometer attached to a homeothermic blanket control unit (Harvard Apparatus Ltd).

After a 15 minute stabilization period, the animals were injected once intravenously with selected doses of each compound, and hemodynamic parameters were continuously monitored for three hours in order to ascertain the duration of action of the compounds under study.

Results

The administration of Compound X in intravenous dosages of 0.1 mg/kg and 1 mg/kg, respectively, caused an immediate, dose related decline in the MAP, in association with a dose-related increase in heart rate. A maximum decline of about 70 mm Hg in the MAP, occurred within the first minute after administration of the Compound X. The effective life of the Compound X which directly correlates with the MAP response returning to 50% of the baseline value, was found to be about fifteen minutes for the 0.1 mg/kg dose and about thirty minutes for the 1.0 mg/kg dose of the Compound X.

With Compound 1, the administration in intravenous dosages of 0.1 mg/kg and 1 mg/kg, caused an immediate, dose-related decline in the MAP, which was associated with a dose-related increase in heart rate. The maximum fall in MAP of about 60 mm Hg occurred within the first minute after the administration of Compound 1. The effective life being a function of the duration of the MAP decline before returning to 50% of the baseline value, for 10 mg/kg and 30 mg/kg of Compound 1, was about 15 minutes and about 30 minutes, respectively.

With Compound 2, an immediate decline in MAP occurred upon administration of both 10 and 30 mg/kg dosages in association with a dose-related increase in heart rate. Following injection of 10 mg/kg of Compound 2, a maximum decline in the MAP of 30 mm Hg occurred within ten minutes after administration of the compound. The effective life being a function of the duration of the MAP decline caused by 10 mg/kg of Compound 2, was about 125 minutes. Following injection of 30 mg/kg of Compound 2, a maximum decline in the MAP of about 30 mm Hg occurred within five minutes after the administration of the compound. Thereafter the MAP appeared to return towards baseline. However, there was a second decline in the MAP at about thirty minutes (which was as pronounced as the first one). The effective lives of the two observed falls in the MAP caused by the 30 mg/kg of Compound 2 were 105–160 minutes, respectively.

With the administration of Compound 3 at a dosage of 30 mg/kg, a small, but immediate decline in the MAP was observed. However, 45 and 120 minutes after injection of Compound 3, there was a gradual decline in the MAP. This delayed decline in the MAP returned towards baseline between 135–165 minutes after injection of Compound 3.

The maximum decline in the MAP of about 30 mm Hg occurred within 75 minutes after administration of the compound. The effective life of the decline in the MAP caused by 30 mg/kg was greater than 105 minutes.

Conclusion

It was confirmed that Compound X caused a substantial dose-related fall in MAP. Similarly to Compound X, Compound 1 causes a dose-related fall of similar magnitude and duration in MAP. Compounds 2 and 3 produced smaller falls in MAP, but their respective duration of action was relatively long. Compound 2 induces a significant, longer-lasting fall in blood pressure, which at dose of 10 mg/kg was not associated with a marked increase in heart rate. The finding that the immediate fall in MAP produced by Compound 2 was not as substantial as that produced by Compound X and Compound 1 offers an advantage in terms of better safety profile by minimizing the stress on the heart due to widely fluctuating changes in the blood pressure. The improved duration provides a more consistent and less drastic blood pressure lowering effect over a longer period of time beneficial to congestive heart failure conditions. In addition, the compounds work to decrease blood pressure by relaxing the tension in the blood vessels to improve blood flow. Such an effect potentially slows or even prevents the loss of heart pumping activity normally associated with congestive heart failure.

EXAMPLE 6

Synthesis of Compound X Diacetate hereinafter referred to as "Compound 4"

A compound of Group 5 wherein $Z_1$ is hydrogen, X is O and each $Z_2$ is an acetyl group, was prepared in the following manner.

In a round-bottom flask, Compound X (400 mg) and pyridine (200 μl) were mixed in 35 ml of anhydrous methylene chloride. 500 μl of acetic anhydride was added to the suspension. The mixture became homogenous in a few hours and the solution was stirred at room temperature overnight. The solvent was condensed and phosphate buffer (0.1 M, pH 7.4) was added to the residue. The mixture was rapidly stirred for 30 minutes, and the mixture was extracted with methylene chloride three times. The combined organic phase was dried over sodium sulfate, and the solvent was removed by vaporization. An oily product, Compound X Diacetate, was obtained. The yield was 340 mg (80%). $^1$H NMR (DMSO-$d_6$): 1.91 (s, (Compound X)-O$^1$COC$\underline{H}_3$), 2.00 (s, (Compound X)-O$^2$COC$\underline{H}_3$), 0.84 (t, (Compound X)-CH$_3$).

EXAMPLE 7

Synthesis of mPEG20K-ester-Compound X Diacetate hereinafter referred to as "Compound 5"

A compound of Group 4 wherein $Z_1$ is a mPEG with a molecular weight of about 20,000 daltons, X is O and each $Z_2$ is an acetyl group, was prepared in the following manner.

In a round bottom-flask, mPEG 20 k daltons (5.2 g), Compound X diacetate (140 mg), 1-hydroxybenzyltriazole (HOBT, 35 mg), 4-(dimethylamino)pyridine (DMAP, 30 mg) and dicyclo-hexylcarbodiimide (DCC, 75 mg) were dissolved in 60 ml of anhydrous methylene chloride. The solution was stirred at room temperature overnight and the solvent removed by vaporization. The residue was mixed with 35 ml of 1,4 dioxane and the insoluble solid was removed by filtration. The solution was concentrated under vacuum and then added to 200 ml of 50:50/ ether:isopropanol. The resulting precipitate was collected by filtration and dried under vacuum. Yield: 4.8 g (92%). $^1$H NMR (DMSO-$d_6$): δ3.5 (br m, PEG), 4.23 (t, -PEGOCH$_2$C$\underline{H}_2$O—CO-(Compound X)), 1.91 (s, (Compound X)-OCOC$\underline{H}_3$), 2.00 (s, (Compound X)-OCOCH3), 0.84 (t, (Compound X)-CH3), 4.77 (s, (Compound X)-C$\underline{H}_2$COOPEG), 7.03 (t, Compound X aromatic proton), 6.7 (d+d, Compound X aromatic proton).

EXAMPLE 8

Anti-Platelet Effects of Compound X and Compounds 4–7 on Human Plasma in Vitro

Introduction

The anti-platelet activity of acetylated Compound X referred hereinafter as Compound 4, and Compounds 5–7 of the present invention on human plasma taken from healthy human volunteers was determined in the following manner, and compared to the anti-platelet activity of the native Compound X. The anti-platelet responses of each compound following incubation with platelet-poor plasma (PPP) and aqueous vehicle (acetate buffer) for various times over a four (4) hour period were also investigated.

Compounds 6 and 7 are respectively, mPEG 20 kDa-amide-Compound X and mPEG20 kDa-amide-Compound X Diacetate and were prepared similarly to Compound 1 of Example 1. Each of Compounds 6 and 7 are compounds of Group 4 wherein $Z_1$ is a mPEG having a molecular weight of about 20,000 daltons and X is NH. For Compound 6, $Z_2$ is hydrogen, while for Compound 7, $Z_2$ is an acetyl group.

Methods

Preparation of Platelet-Rich Plasma (PRP)

Blood from healthy human volunteers who had not taken any medicine for at least 14 days was collected by venopuncture into 3.15% (w/v) tri-sodium citrate (9:1 v/v). The blood was centrifuged at 800 g for 15 minutes to produce PRP. The PRP was further centrifuged at 12,000 g for 1 minute to produce PPP. A total of 12 volunteers donated blood for the study.

Photometric Measurement of Platelet Aggregation

Platelet aggregation was studied using a dual channel Payton aggregometer calibrated with PRP (0%) and PPP (100%) with respect to the degree of light transmission. Aliquots of PRP (500 μl) were added to siliconized cuvettes, stirred (1000 revs/min) and warmed to 37° C. The platelets were incubated for 1 minute to establish a stable baseline prior to investigation. A submaximal concentration of the aggregating agent collagen (1 μg/ml) was added to the PRP and the platelet aggregation was monitored as the increase in light transmission observed over a 4 minute period.

Anti-Aggregatory Activity

Compound X (1–100 ng/ml), Compound 4 (1–300 ng/ml) and the PEG conjugated derivatives, Compound 5–7 (0.1–10 mg/ml) were each incubated with PRP for 1 minute prior to the addition of collagen (1 μg/ml), a clotting agent. The percentage inhibition of the platelet aggregation was calculated using the peak increase in light transmission observed over the 4 minute period following addition of collagen, as compared to that of control. This experiment was repeated using PRP from at least three human volunteers for each compound under study.

Anti-Aggregatory Response After Incubation with Aqueous Vehicle and PPP

In separate experiments, concentrations of Compound X (30 and 300 ng/ml), Compound 4, and Compounds 5–7, were incubated with 500 μPPP or aqueous vehicle (acetate buffer) for various times including 15 minutes, 1 hour, and 4 hours at 37° C. After the incubation period, an aliquot of the PPP or aqueous vehicle (50 µl) was added to fresh PRP (450 µl) for determination of anti-platelet activity. This experiment was repeated using PPP from at least three human volunteers for each compound.
Results
Effects of Compound X on Platelet Aggregation Compound X (1–100 ng/ml), incubated with PRP for one (1) minute, caused a concentration dependent inhibition of collagen-induced platelet aggregation. At the higher concentrations (30 and 100 ng/ml), Compound X completely inhibited the aggregation response. The concentration of Compound X inhibiting aggregation by 50% ($IC_{50}$) was 19±1 ng/ml.
Effects of Compound 4 on Platelet Aggregation Compound 4, the Compound X diacetate (1–300 µg/ml), incubated with PRP for one (1) minute, cause a concentration-dependent inhibition of platelet aggregation. At the highest concentration (300 µg/ml), Compound 4 completely inhibited the aggregation response to collagen, with an inhibiting aggregation by 50% concentration of 68±2 µg/ml. By comparison to the anti-aggregatory activity of Compound X, Compound 4 was some $3 \times 10^3$ times less active in inhibiting platelet aggregation after one (1) minute of incubation.

The anti-platelet activity of Compound 4 increased over the first 15 minutes following incubation with PPP. After 15 minutes, the activity had increased by some 10-fold, with an $IC_{50}$ of 5±0.2 µg/ml. This effect was also observed during incubation of the compound in saline. However, no further increase in activity was observed when incubated in PPP for up to 4 hours.
Effects of Compound 5 on Platelet Aggregation Compound 5, at the highest concentration evaluated (10 mg/ml), caused approximately ten percent (10%) inhibition of platelet aggregation when incubated with PRP for one (1) minute. Lower concentrations of Compound 5 had no significant anti-platelet activity after this one (1) minute incubation.

The activity of high concentrations of Compound 5 increased in a time-dependent manner following incubation with PPP for one (1) hour and four (4) hours. This activity increased by greater than ten (10)-fold when incubated for four (4) hours in PPP, with an $IC_{50}$ of 513±18 µg/ml. However, incubation of Compound 5 with aqueous vehicle had no such effect on anti-platelet activity at any time point tested.
Effects of Compound 6 on Platelet Aggregation Compound 6 (0.1–3 mg/ml), incubated with PRP for one (1) minute, caused a concentration-dependent inhibition of platelet aggregation. At the highest concentration (3 mg/ml), Compound 6 near-maximally inhibited the aggregation response. The $IC_{50}$ of Compound 6 was 600±34 µg/ml.

Incubation of Compound 6 (100 µg/ml) with PPP for four (4) hours, at a concentration that was ineffective after one (1) minute, caused an increase in activity, reaching 85% inhibition of platelet aggregation. The $IC_{50}$ of Compound 6 after four (4) hour incubation was 60±5 µg/ml. Because of the weak activity even after this period of incubation, no further concentrations were evaluated.

Incubation of Compound 6 with aqueous vehicle had no effect on anti-platelet activity at any time point tested.
Effects of Compound 7 on Platelet Aggregation Compound 7 (10 mg/ml), incubated with PRP for one (1) minute, at the highest concentration, did not significantly inhibit the aggregation response.

Incubation of Compound 7 (10 mg/ml) with PPP or aqueous vehicle for four (4) hour, showed no increase in activity. Because of the weak activity even after this period of incubation, no further concentrations were evaluated.
Conclusion The present study confirms the potent platelet anti-aggregatory activity in vitro of the benzindene derivative of prostacyclin, Compound X, in human platelet-rich plasma, as determined in an optical aggregometer. The potency of this compound after a one (1) minute incubation with the platelet suspension in the present study is similar to that previously reported in Example 4. As in the previous study, the anti-platelet activity was not affected by incubation with platelet-free plasma or aqueous vehicle for periods up to four (4) hours at 37° C., confirming its chemical stability under physiological conditions.

The findings of the present study indicate that Compound X has significantly greater anti-plaielet activity than the diacetate derivative, Compound 4, the diacetate being about 3,000 times less active. This acetylated derivative did increase its activity some 10-fold on incubation with plasma or aqueous vehicle over an initial ten (10) minute period, but this increase in activity was no greater after four (4) hours of incubation. The mechanism of this early increase in activity may reflect a transient instability of the diacetate when incubated in the PPP media.

The present study also indicates that Compound X had significantly greater anti-platelet activity than Compounds 4–7. Compound 6 was the most active of the three PEG conjugated derivatives (Compounds 5–7), after incubation with the platelet-rich plasma for one (1) minute, but was considerably less potent than Compound X, being some $3 \times 10^4$ fold less active.

The anti-platelet activity of Compounds 5–7 were variably affected by incubation with platelet-poor plasma (PPP) for periods up to four (4) hours. Time points greater than four (4) hours could not be tested using human plasma in vitro because the platelet aggregation response declines rapidly after 6 hours post-collection. The activity of Compounds 5 and 6 increased over the four (4) hours of incubation by 10-fold or greater, an effect not seen when incubated in saline. These findings suggest that the active moiety of these PEG conjugated derivatives (Compounds 5–7) is released in a time-dependent manner by enzymes present in human plasma, after incubation at 37° C. over four (4) hours, i.e. hydrolysis of the ester and acetate groupings respectively on these molecules in human plasma. However, it should be noted that the increased in activity observed with the compounds was substantially lower than that observed with some of the compounds from the study in Example 4.

These findings with Compounds 5–7 indicate that inclusion of the PEG moiety of 20,000 daltons molecular weight, along with acetate groupings, reduces the anti-aggregatory activity of Compound X. However, the activity of Compounds 5 and 6 increases on incubation over a four (4) hour period with human plasma, indicating hydrolysis of these substituent groupings. A ten-fold increase in activity of these compounds was observed following incubation over a 4 hour period with human plasma, but not when incubated in buffer alone, indicating enzymatic hydrolysis of the ester and amide linkages in these derivatives, with release of the active moiety. The present findings confirm the creation of slow-release derivatives of Compound X based on PEG substitution, that can be activated in human plasma. Such anti-aggregatory response is beneficial in maintaining a lower vascular resistance in the systemic and pulmonary systems for an improved blood flow especially in patients with congestive heart failure.

EXAMPLE 9

Systemic Hemodynamic Effects of Compound X and Compounds 4–7 in Anesthetized Rats in Vivo Introduction In this study, cardiovascular activity of Compounds 4–7 were observed in thiopentone-anesthetized rat. The effects of these compounds on blood pressure (BP) and heart rate following bolus intravenous injection were determined. The time for onset and maximal response were noted, as well as the time taken for the response to return towards the baseline. Each compound was administered as a single dose to individual animals, to establish the dose-response curve.

Among its other effects, Compounds 4–7 in vitro induce a concentration-dependent relaxation of mesenteric arteries which causes a measurable decrease in mean arterial pressure (MAP) when administered intravenously in anesthetized rats. To confirm the improvement of the effective life of Compounds 4–7 over the Compound X, Applicants sought to measure the changes in MAP over time to extrapolate the effective life of the compounds which is defined as the time taken for the response to return to 50% of the baseline value. Among other effects, lowering of the blood pressure inside the blood vessels is beneficial for the treatment of congestive heart failure by reducing the vascular resistance of the blood flow which substantially reduces the work load imposed on the heart. As a result, the heart does not have to work as hard to pump blood through the vessels.

Materials and Methods

This study involved the use of male Wistar rats anaesthetized with thiopentone sodium (Intraval®, 120 mg kg$^{-1}$ i.p.). The trachea was cannulated to facilitate breathing. The right carotid artery was cannulated and connected to a pressure transducer (Spectramed P23XL), for the measurement of mean arterial pressure (MAP) and heart rate (HR) which were continuously recorded on a 4-channel Grass 7D polygraph recorder (Grass, Mass., USA). The left femoral vein or the right jugular vein was cannulated for the administration of drugs. Body temperature was maintained at 37±1° C. by means of a rectal probe thermometer attached to a homeothermic blanket control unit (Harvard Apparatus Ltd).

After a 15 minute stabilization period, the animals were injected with single intravenous injections of selected doses of native Compound X, and Compounds 4–7, respectively, and hemodynamic parameters were continuously monitored for three hours in order to ascertain the duration of action of the compounds under study.

Results

The administration of Compound 4 in the intravenous dosages of 1, 3, and 10 mg/kg, respectively, caused a rapid, dose-related fall in MAP, which was associated with a dose-dependent increase in heart rate. Following injection of 1 mg/kg, a maximum fall in MAP of about 30 mm Hg occurred 30 minutes after administration of the compound. The effective life of the fall in MAP caused by 1 mg/kg of compound 4 was about 110 minutes.

Administration of a dose of Compound X (1 mg/kg i.v.) caused a similar, maximal fall in MAP to the highest dose of Compound 4 (10 mg/kg i.v.). When compared to Compound X, the fall in MAP caused by Compound 4 was of a substantially longer duration, with a effective life of over 90 minutes compared to 30 minutes for Compound X. The duration of effects of Compound 4 was longer than that elicited by a 10-fold maximal dose of Compound X. The findings indicate that the increased duration of action as observed with this derivative, cannot be achieved by supramaximal doses of Compound X. Furthermore, the tachycardia caused by Compound 4 was slower in onset than the tachycardia caused by Compound X. It should be noted that the tachycardia caused by Compound 4 was still significant at 3 hours after injection of the compound.

Administration of Compound 5 (3, 10, and 30 mg/kg i.v.) caused a dose-related fall in MAP which was less pronounced than that produced by Compound 4 or Compound X, and which was not associated with a significant increase in heart rate. The response reached its maximum after 15 minutes, with a very long duration of action, with a effective life of about 120 minutes.

Administration of Compound 6 (3, 10, and 30 mg/kg i.v.) caused an immediate dose-related fall in MAP, which was slow in onset and at higher dosages, appeared to be maximal at 3 hours after injection of the compound. The maximum fall was about 60 mm Hg within 10 minutes. However, the duration of the initial phase of this response was short, and was followed by a slower phase of recovery of blood pressure towards the resting values. Interestingly, Compound 6 did not cause a significant change in heart rate.

Compound 4 and Compound 6 both resulted in rapid and substantial falls in MAP. However, in the case of Compound 4, the drop in MAP was also accompanied by a pronounced increase in heart rate. Although the fall in MAP produced by Compound 4 was of longer duration, the rapid fall in MAP and the resultant tachycardia would be disadvantageous as to its safety profile.

In contrast, Compound 7 (3, 10 and 30 mg/kg i.v.) caused a gradual fall in MAP which reached its plateau levels only after 135–165 minutes. The gradual fall was progressive and appeared to reach a maximum of about 30 mm Hg at the end of the 3 hour experimental period. This fall in MAP was not associated with tachycardia.

Conclusion

The cardiovascular profile of the present compounds permits some definition of the structure-activity relationship, and hence design of Compound X derivatives that exhibit a long duration of action. In addition, it appears such compounds may be formulated with a slow onset of action that would minimize the possibility of any initial hypotensive crisis that could potentially stress and damage the heart. Comparison of the profile of compounds conjugated to either 5,000 or 20,000 daltons PEG suggests that although there appears to be no difference in MAP profile or the duration of hypotensive effects with either PEG size, there is a trend towards less of an effect on heart rate with the compounds containing 20,000 daltons PEG. The potential clinical advantage associated with the absence of reflex tachycardia requires further consideration.

Comparison of the profiles for compounds linked to the PEG substituent via either the amide or ester linkage suggests that the fall in MAP for the amide is slower in onset than that observed with the ester, and was not observed to trigger reflex tachycardia.

EXAMPLE 10

Systemic Hemodynamic Effects of Subcutaneous Administration of Compound 2 in Anesthetized Rat Compound 2 was evaluated following subcutaneous administration. Male Wistar rats (250–330 g) were anesthetized with thiopentone sodium (INTRAVAL®, 120 mg/kg i.p.). The trachea was cannulated to facilitate respiration. The right carotid artery was cannulated and connected to a pressure transducer (Spectramed P23XL), for the measurement of mean arterial pressure (MAP) and heart rate (HR) which were continuously recorded on a 4-channel Grass 7D polygraph recorder (Grass, Mass., U.S.A.). Body temperature was maintained at 37±1° C. by means of a rectal probe thermometer attached to a homeothermic blanket control unit (Harvard Apparatus Ltd.). After a 15 minute stabilization period, compound 2 was injected as a bolus subcutaneously in the neck.

Subcutaneous administration of Compound 2 (30 mg/kg s.c.) caused a substantial fall in MAP, which was slow in onset and reached a maximum at 45 minutes after injection of the compound. In addition, Compound 2 caused an increase in heart rate. When compared to intravenous administration of Compound 2 (30 mg/kg i.v.) of Example 5, the long-lasting fall in MAP caused by the subcutaneous administration was more pronounced, but slower in onset. At 3 hours, a larger magnitude was produced that was of larger magnitude than that produced by intravenous administration of the same compound. A further analysis of the subcutaneous administration of this and other compounds is warranted.

EXAMPLE 11

Systemic Hemodynamic Effects of Subcutaneously Administered Compound X,. Compound 4, Compound 7 and mPEG5 kDa-amide-Compound X Diacetate in Anesthetized Rats in Vivo Compound X, Compound 4, Compound 7 and mPEG5 kDa-amide-Compound X Diacetate, hereinafter referred to as Compound 8, were evaluated following subcutaneous administration. Male Wistar rats (250–330 g) were anesthetized with thiopentone sodium (INTRAVAL®, 120 mg/kg i.p.). The trachea was cannulated to facilitate respiration. The right carotid artery was cannulated and connected to a pressure transducer (Spectramed P23XL), for the measurement of mean arterial pressure (MAP) and heart rate (HR) which were continuously recorded on a 4-channel Grass 7D polygraph recorder (Grass, Mass., U.S.A.). Body temperature was maintained at 37±1°C. by means of a rectal probe thermometer attached to a homeothermic blanket control unit (Harvard Apparatus Ltd.). After a 15 minute stabilization period, native Compound X, Compound 4, Compound 7 or Compound 8 were injected as a bolus subcutaneously in the neck.

Compound 8 referred was prepared similarly to Compound 1 of Example 1. Compound is a compound of Group 4 wherein $Z_1$ is a mPEG having a molecular weight of about 20,000 daltons, X is NH and $Z_2$ is an acetyl group.

Results

Administration of Compound 4 in the subcutaneous dosages of 1, 3, and 10 mg/kg, respectively, caused a dose-related fall in MAP, which was also associated with a dose-dependent increase in heart rate. Following injection of 1 mg/kg, a maximum fall in MAP of about 26 mm Hg occurred 60 minutes after administration of the compound with another fall occurring 210 minutes to 28 mm Hg. The effective lives of the fall in MAP caused by each of the three respective dosages of Compound 4 were >300, >330 and >300 minutes, respectively. (See Table 5).

Administration of Compound X (0.1, 0.3 and 1 mg/kg s.c.) caused a rapid dose-related fall in MAP, which was associated with a dose-dependent increase in heart rate. (See Table 4). Following subcutaneous injection of 1 mg/kg, a maximum fall in MAP of about 70 mm Hg occurred 15 minutes after administration of the compound. When compared to Compound X, the fall in MAP caused by Compound 4 was of a substantially longer duration. The tachycardia caused by Compound 4 was substantially slower in onset than the tachycardia caused by Compound 4. It should be noted that the tachycardia caused by Compound 4 was still significant for the 10 mg/kg dosage at 6 hours after injection of the compound. At lower dosages, the heart rate stabilized at about 5 minutes and 45 minutes after injection, for 1 mg/kg and 3 mg/kg, respectively.

Administration of Compound 7 (3, 10 and 30 mg/kg) caused a gradual, progressive dose-related fall in MAP, which continued to fall 6 hours after the injection. The magnitude of activity was less than the native Compound X and Compound 4. The maximum falls in MAP were 35, 29 and 25 mm Hg for 3, 10 and 30 mg/kg dosages, respectively. All the maximum falls occurred at about 330 to 360 minutes after injection. (See Table 6).

Administration of Compound 8 (3, 10 and 30 mg/kg s.c.) caused a slow dose related fall in MAP and appeared to reach a maximum of about 24 mm Hg for the maximal dose at about 240 minutes after the injection. The effective life was greater than 120 minutes. (See Table 7).

Such a time-extended drop in arterial pressure contributes substantially to the reduction of vascular resistance thereby alleviating the conditions associated with congestive heart failure over a longer period of time.

TABLE 4

Mean Arterial Pressure (mm Hg) Measured over a 6 hour time course for Compound X (Subcutaneous Administration)

| Time | | Compound X | | |
|---|---|---|---|---|
| (min) | Vehicle | 0.1 mg/kg | 0.3 mg/kg | 1 mg/kg |
| 0 | 121 ± 6 | 123 ± 6 | 121 ± 6 | 134 ± 6 |
| 1 | 127 ± 4 | 111 ± 6 | 91 ± 11 | 82 ± 4 |
| 5 | 124 ± 5 | 83 ± 7 | 70 ± 9 | 67 ± 5 |
| 10 | 124 ± 3 | 81 ± 6 | 69 ± 11 | 67 ± 6 |
| 15 | 124 ± 2 | 78 ± 4 | 71 ± 11 | 63 ± 7 |
| 30 | 122 ± 3 | 82 ± 6 | 80 ± 11 | 67 ± 4 |
| 60 | 116 ± 4 | 90 ± 7 | 88 ± 9 | 75 ± 3 |
| 120 | 114 ± 5 | 97 ± 10 | 101 ± 12 | 88 ± 5 |
| 180 | 112 ± 5 | 101 ± 13 | 111 ± 10 | 98 ± 6 |
| 240 | — | 102 ± 13 | 103 ± 8 | 93 ± 8 |
| 360 | — | 100 ± 13 | 92 ± 5 | 95 ± 9 |
| $A_{max}^{Time}$ | $9 ± 4^{180}$ | $46 ± 5^{15}$ | $52 ± 12^{10}$ | $71 ± 8^{15}$ |
| $t_{½}$ | — | 165 | 80–110 | 135–290 |
| n | 3 | 5 | 5 | 5 |

TABLE 5

Mean Arterial Pressure (mm Hg) Measured over a 6 hour time course for Compound 4 (Subcutaneous administration).

| Time | | Compound 4 | | |
|---|---|---|---|---|
| (min) | Vehicle | 1 mg/kg | 3 mg/kg | 10 mg/kg |
| 0 | 121 ± 6 | 115 ± 11 | 119 ± 7 | 128 ± 6 |
| 1 | 127 ± 4 | 116 ± 9 | 116 ± 7 | 116 ± 7 |
| 5 | 124 ± 5 | 110 ± 9 | 96 ± 6 | 107 ± 7 |
| 10 | 124 ± 3 | 104 ± 8 | 86 ± 6 | 92 ± 8 |
| 15 | 124 ± 2 | 99 ± 6 | 82 ± 6 | 95 ± 5 |
| 30 | 122 ± 3 | 93 ± 4 | 78 ± 4 | 86 ± 6 |
| 60 | 116 ± 4 | 90 ± 5 | 82 ± 4 | 83 ± 5 |
| 120 | 114 ± 5 | 91 ± 5 | 86 ± 3 | 82 ± 6 |
| 180 | 112 ± 5 | 92 ± 5 | 87 ± 4 | 86 ± 5 |
| 240 | — | 87 ± 3 | 86 ± 4 | 86 ± 6 |
| 360 | — | 94 ± 3 | 86 ± 5 | 81 ± 9 |
| $A_{max}^{Time}$ | $9 ± 4^{180}$ | $26 ± 6^{60}$, $(28 ± 7^{210})$ | $41 ± 4^{30}$ | $45 ± 5^{60}$, $(48 ± 6)^{150}$ |
| $t_{½}$ | — | >300 | >330 | >300 |
| n | 3 | 5 | 5 | 5 |

TABLE 6

Mean Arterial Pressure (mm Hg) Measured over a 6 hour time course for Compound 7 (Subcutaneous administration).

| Time | mPEG | Compound 7 | | |
|---|---|---|---|---|
| (min) | 20 kDa | 3 mg/kg | 10 mg/kg | 30 mg/kg |
| 0 | 135 ± 5 | 136 ± 9 | 133 | 136 ± 5 |
| 1 | 138 ± 4 | 141 ± 7 | 132 | 136 ± 3 |
| 5 | 135 ± 6 | 139 ± 6 | 130 | 138 ± 4 |
| 10 | 139 ± 3 | 133 ± 7 | 128 | 134 ± 4 |
| 15 | 136 ± 5 | 135 ± 8 | 128 | 134 ± 4 |
| 30 | 130 ± 8 | 127 ± 9 | 123 | 130 ± 2 |
| 60 | 127 ± 9 | 117 ± 6 | 114 | 131 ± 3 |
| 120 | 128 ± 15 | 114 ± 7 | 114 | 127 ± 4 |
| 180 | 123 ± 10 | 104 ± 9 | 114 | 117 ± 5 |
| 240 | 113 ± 7 | 106 ± 11 | 111 | 115 ± 5 |
| 360 | 112 ± 10 | 104 ± 7 | 104 | 111 ± 4 |
| $A_{max}^{Time}$ | 27 ± $5^{330}$ | 35 ± $8^{330}$ | 29 ± $5^{360}$ | 25 ± $9^{360}$ |
| $t_{½}$ | — | — | — | — |
| n | 5 | 5 | 5 | 5 |

TABLE 7

Mean Arterial Pressure (mm Hg) Measured over a 6 hour time course for Compound 8 (Subcutaneous Administration)

| Time | mPEG | Compound 8 | | |
|---|---|---|---|---|
| (min) | 5k | 3 mg/kg | 10 mg/kg | 30 mg/kg |
| 0 | 113 ± 11 | 119 ± 11 | 116 ± 6 | 134 ± 8 |
| 1 | 111 ± 14 | 124 ± 11 | 117 ± 12 | 133 ± 8 |
| 5 | 110 ± 13 | 122 ± 10 | 119 ± 7 | 135 ± 8 |
| 10 | 109 ± 15 | 121 ± 9 | 115 ± 5 | 132 ± 8 |
| 15 | 103 ± 14 | 122 ± 9 | 116 ± 4 | 132 ± 7 |
| 30 | 105 ± 12 | 119 ± 10 | 105 ± 9 | 127 ± 8 |
| 60 | 103 ± 13 | 123 ± 11 | 110 ± 1 | 121 ± 8 |
| 120 | 97 ± 8 | 122 ± 11 | 108 ± 2 | 113 ± 8 |
| 180 | 98 ± 10 | 119 ± 9 | 105 ± 2 | 116 ± 8 |
| 240 | — | 112 ± 7 | 108 ± 6 | 109 ± 5 |
| 360 | — | 110 ± 15 | 113 ± 5 | 111 ± 5 |
| $A_{max}^{Time}$ | — | 14 ± $12^{270}$ | 11 ± $5^{30}$ | 24 ± $7^{240}$ |
| $t_{½}$ | 17 ± $4^{120}$ | — | — | >120 |
| n | 4 | 5 | 5 | 5 |

EXAMPLE 12

Synthesis of mPEG350 Da-amide-Compound X Diacetate hereinafter referred to as "Compound 9"

A compound of Group 4 wherein $Z_1$ is a mPEG with a molecular weight of about 350 daltons, X is NH and each $Z_2$ is an acetyl group, was prepared in the following manner.

In a round-bottom flask, Compound X (400 mg), mPEG (350 Da) amine (360 mg), HOBT (15 mg), and DCC (267 mg) were mixed with 20 ml of anhydrous methylene chloride and the mixture was stirred at room temperature overnight. The insoluble solid was removed by filtration and the organic solution was washed with 5 wt % sodium bicarbonate solution. The organic phase was dried over sodium sulfate and the solvent removed under vacuum. The resulting product was dissolved in 10 ml of acetonitrile and the insoluble solid was removed by filtration. To the solution was added acetic anhydride (3 ml) and pyridine (0.3 ml). The resulting solution was heated at 40° C. overnight. To the solution was added 300 ml of 5 wt % sodium bicarbonate solution and the mixture was stirred 30 minutes at room temperature. The mixture was extracted with methylene chloride and the organic phase was washed with phosphate buffer (0.1 M, pH 2) and dried over sodium sulfate. The solvent was removed and the product dried under vacuum. The yield was 600 mg (70%). $^1$H NMR (DMSO-d6): δ3.5 (br m, PEG), 7.897 (t, -PEGN$\underline{H}$-CO-(Compound X)), 1.91 (s, (Compound X)-O$^1$COC$\underline{H}_3$), 2.00 (s, (Compound X)-O$^2$COC$\underline{H}_3$), 0.864 (t, (Compound X)-C$\underline{H}_3$), 4.436 (s, (Compound X)-C$\underline{H}_2$CONHPEG), 7.045 (t, Compound X aromatic proton), 6.7 (d+d, Compound X aromatic compound).

EXAMPLE 13

Synthesis of mPEG350 Da-ester-Compound X Diacetate hereinafter referred to as "Compound 10"

A compound of Group 4 wherein $Z_1$ is a mPEG with a molecular weight of about 350 daltons, X is O and each $Z_2$ is an acetyl group, was prepared in the following manner.

In a round-bottom flask, Compound X (3 g) and triethylamine (TEA, 1.5 μl) were mixed in 100 ml of anhydrous acetonitrile. To the solution was added 3 ml of acetyl chloride. The mixture was stirred at room temperature overnight. The solution was then mixed with 5 wt % sodium bicarbonate solution and stirred 30 minutes at room temperature. The aqueous phase was extracted with methylene chloride. The organic phase was washed with phosphate buffer (0.1 M, pH 2) and then dried over sodium sulfate. The yield was 3.3 g (80%). $^1$H NMR(DMSO-d$_6$): 1.91 (s, (Compound X)-O$^1$COC$\underline{H}_3$), 2.00 (s, (Compound X)-O$^2$COC$\underline{H}_3$), 0.84 (t, (Compound X)-CH$_3$).

In a round-bottom flask, mPEG (350 Da) (550 mg), Compound X diacetate from the previous step (750 mg), HOBT (60 mg), DMAP (150 mg), and DCC (375 mg) were dissolved in 30 ml of anhydrous methylene chloride. The solution was stirred at room temperature overnight. The insoluble solid was removed by filtration and the solution was washed with 5 wt % sodium bicarbonate solution and phosphate buffer (0.1 M, pH 2). The organic phase was dried over sodium sulfate and concentrated under vacuum. The resulting product was dissolved in 10 ml of acetonitrile and the insoluble solid was removed by filtration. The solvent was removed by vaporization and the product was obtained as a clear oil. The yield was 1 g (76 %). $^1$H NMR(DMSO-d$_6$): δ3.5 (br m, PEG), 4.23 (t, -PEGOCH$_2$C$\underline{H}_2$O—CO-(Compound X)), 1.91 (s, (Compound X)-O$^1$COC$\underline{H}_3$), 2.00 (s, (Compound X)-O$^2$COC$\underline{H}_3$), 0.84 (t, (Compound X)-CH$_3$), 4.77 (s, (Compound X)-C$\underline{H}_2$COOPEG), 7.03 (t, Compound X aromatic proton), 6.7 (d+d, Compound X aromatic proton).

EXAMPLE 14

Evaluation of the Effects of mPEG 350 Da-amide-Compound X Diacetate on Systemic Hemodynamics in Anesthetized Rats In Vivo In this study, the cardiovascular activity of novel, lower polyethylene glycol (PEG) derivatives of the chemically stable benzindene analog of prostacyclin, Compound X following both intravenous and oral administration in rats was evaluated. The mPEG350 Da-amide-Compound X Diacetate, or Compound 9 hereinafter, was synthesized in an attempt to produce a derivative that would be effective by the oral route. An orally effective analog would develop further the clinical potential of stable prostacyclin analogs in a number of therapeutic utilities.

Previous studies have evaluated a number of derivatives of Compound X linked to moieties of varying weights. In those studies high molecular weight polymers of PEG of 5,000 and 20,000 daltons were attached to different regions of the native compound by ester or amide linkages, while the effects of acetylating the free hydroxyl groups were also studied. Their systemic hemodynamic profile were studied in the anesthetized rat following intravenous bolus administration, and in the later study, following subcutaneous bolus injection. The current study has evaluated the actions of the 350 molecular weight PEG derivative on rat systemic arterial blood pressure following either intravenous or oral administration.

Compound Under Evaluation

The compound used in the present study was the acetylated mPEG 350 Da Compound X-amide (mPEG 350-NHCO-Compound X-Ac) hereinafter referred to as "Compound 9", in which the PEG of 350 daltons molecular weight is linked to the carboxylic group of Compound X through an amide linkage and the hydroxyl groups of Compound X are acetylated.

General Methodology

The series of studies described herein are on the cardiovascular activity of these compounds in the thiopentone-anesthetized rat. In these studies, the effects of the Compound 9 on blood pressure (BP) and heart rate following bolus intravenous and oral administration were observed. The time for onset and maximal response was determined, as well as the time taken for the response to return towards 50% of the baseline value. Each compound was administered as a single dose to individual animals in the group, to establish the dose-response relationship, and the cardiovascular parameters determined for 3 hours after the intravenous administration and 6 hours after the oral administration.

Male Wistar rats (250–330 g) were anesthetized with thiopentone sodium (INTRAVAL®, 120 mg kg$^{-1}$ i.p.). The trachea was cannulated to facilitate respiration. The right carotid artery was cannulated and connected to a pressure transducer (Spectramed P23XL), for the measurement of mean arterial pressure (MAP) and heart rate (HR) which were continuously recorded on a 4-channel Grass 7D polygraph recorder (Grass, Mass., U.S.A.). The left femoral vein or the right jugular vein was cannulated for the administration of drugs. Body temperature was maintained at 37±1° C. by means of a rectal probe thermometer attached to a homeothermic blanket control unit (Harvard Apparatus Ltd.).

Methodology for Intravenous Administration

The Compound 9 was dissolved in absolute ethanol to give a stock solution of 200 mg/ml, which was stored in the freezer at −20° C. Aliquots of the stock solution were removed immediately prior to use, and dissolved in saline. Rats receiving 3, 10, and 30 mg/kg of the Compound 9 thus received 1.5%, 5% and 15% of ethanol in 0.3 ml. In the control group, the rats received the highest concentration of ethanol, 0.3 ml i.v. of an ethanolic solution of 15%.

After a 15-minute stabilization period, the Compound 9 (3, 10 and 30 mg/kg) was administered as an intravenous bolus.

Methodology for Oral Administration

A rubber catheter was positioned in the stomach (via the esophagus) to facilitate oral dosing. After a 20 minute stabilization period, Compound 9 was administered as a total of 1 ml bolus down this tube.

The Compound 9 was dissolved in absolute ethanol to give a stock solution of 200 mg/ml, which was stored in the freezer at −20° C. Aliquots of the stock solution were removed immediately prior to use, and dissolved in saline. Rats received 30 mg/kg of the Compound 9, thus 15% of ethanol in 1.0 ml. In the control group, the rats received 1 ml of an ethanolic solution of 15%.

The study was conducted in either non-fasted animals, that had food in the stomach at post mortem, or rats that had had food removed some 15 hours prior to investigation.

Results of the Intravenous Administration

In the anesthetized rat, intravenous injection of Compound 9 (3, 10 and 30 mg/kg i.v.) caused a rapid dose-dependent fall in MAP (See Table 8A), but had no significant effect on heart rate. With the maximal dose, this hypotensive response reached its peak value well within 15 minutes, but had a long duration of action, with a effective life of at least 120 minutes. It should be noted that the higher doses of the Compound 9 appeared to cause a transient fall in heart rate. (See Table 8B).

Such a time-extended drop in arterial pressure observed herein, contributes substantially to the reduction of vascular resistance thereby alleviating the conditions associated with congestive heart failure over a prolonged duration.

TABLE 8A

Dose Response from Intravenous Administration of Compound 9 (Mean Arterial Pressure, mm Hg)

| | | Compound 9 | | |
|---|---|---|---|---|
| Time (min) | Ethanol Vehicle | 3 mg/kg | 10 mg/kg | 30 mg/kg |
| 0 | 131 ± 10 | 121 ± 7 | 128 ± 10 | 137 ± 7 |
| 1 | 123 ± 10 | 117 ± 9 | 109 ± 10 | 92 ± 8 |
| 5 | 123 ± 10 | 111 ± 6 | 114 ± 6 | 96 ± 8 |
| 10 | 122 ± 10 | 108 ± 4 | 114 ± 6 | 99 ± 6 |
| 15 | 122 ± 10 | 109 ± 4 | 112 ± 4 | 101 ± 5 |
| 30 | 123 ± 10 | 110 ± 6 | 109 ± 6 | 103 ± 8 |
| 45 | 122 ± 9 | 110 ± 3 | 108 ± 4 | 106 ± 7 |
| 60 | 118 ± 9 | 110 ± 5 | 100 ± 4 | 105 ± 3 |
| 75 | 117 ± 9 | 112 ± 5 | 105 ± 7 | 105 ± 5 |
| 90 | 115 ± 8 | 108 ± 7 | 106 ± 5 | 104 ± 5 |
| 105 | 115 ± 7 | 107 ± 6 | 108 ± 6 | 104 ± 3 |
| 120 | 116 ± 9 | 107 ± 7 | 105 ± 5 | 105 ± 4 |
| 135 | 112 ± 8 | 106 ± 6 | 106 ± 6 | 107 ± 4 |
| 150 | 108 ± 7 | 107 ± 7 | 107 ± 5 | 107 ± 4 |
| 165 | 108 ± 7 | 110 ± 8 | 105 ± 4 | 107 ± 3 |
| 180 | 109 ± 8 | 113 ± 8 | 108 ± 5 | 109 ± 4 |
| $\Delta_{max}^{Time}$ | 23 ± 4$^{150}$ | 15 ± 3$^{105}$ | 28 ± 11$^{60}$ | 45 ± 4$^{1}$ |
| t½ | — | — | — | — |
| n | 6 | 5 | 5 | 5 |

TABLE 8B

Dose Response from Intravenous Adminstration of Compound 9 (Heart Rate)

| | | Compound 9 | | |
|---|---|---|---|---|
| Time (min) | Ethanol Vehicle | 3 mg/kg | 10 mg/kg | 30 mg/kg |
| 0 | 379 ± 23 | 333 ± 8 | 361 ± 18 | 391 ± 19 |
| 1 | 380 ± 22 | 354 ± 14 | 313 ± 8 | 318 ± 23 |
| 5 | 394 ± 22 | 364 ± 18 | 331 ± 13 | 322 ± 19 |
| 10 | 392 ± 25 | 351 ± 19 | 339 ± 13 | 348 ± 14 |
| 15 | 393 ± 28 | 346 ± 22 | 344 ± 17 | 359 ± 17 |
| 30 | 392 ± 30 | 341 ± 23 | 322 ± 13 | 384 ± 21 |
| 45 | 394 ± 30 | 353 ± 20 | 322 ± 12 | 395 ± 13 |
| 60 | 385 ± 29 | 337 ± 13 | 358 ± 17 | 390 ± 11 |
| 75 | 380 ± 25 | 355 ± 18 | 346 ± 12 | 387 ± 9 |
| 90 | 393 ± 24 | 352 ± 18 | 356 ± 27 | 378 ± 11 |
| 105 | 372 ± 26 | 347 ± 17 | 342 ± 8 | 376 ± 11 |
| 120 | 367 ± 25 | 346 ± 20 | 363 ± 14 | 371 ± 13 |
| 135 | 358 ± 25 | 350 ± 15 | 347 ± 7 | 371 ± 10 |
| 150 | 363 ± 25 | 353 ± 15 | 376 ± 21 | 373 ± 13 |
| 165 | 363 ± 26 | 361 ± 16 | 336 ± 15 | 368 ± 12 |
| 180 | 353 ± 25 | 358 ± 10 | 364 ± 20 | 368 ± 12 |
| n | 6 | 5 | 5 | 5 |

Results of the Oral Administration

In the anesthetized rats, oral administration of Compound 9 (30 mg/kg) to either fed or starved rats caused a fall in MAP, which was slow in onset, progressive and of long duration (See Table 9A). The fall in MAP reached its peak after 120 minutes, with the MAP remaining depressed at the end of the 6 hour observation period. A maximum fall in MAP of about 33 mm Hg was observed at the end of the observation period at 6 hours. It should be noted, however, that the vehicle containing ethanol (0.3 ml of 15% ethanol) also caused a small, gradual fall in MAP, which was slow in onset and reached a maximum of 20 mm Hg after 6 hours (See Table 9A). There appeared to be no difference between the vasodepressor response to the Compound 9 in either the fed or starved rats.

The ethanolic vehicle also caused a progressive fall in heart rate (see Table 9B), which was more pronounced than any fall in heart rate caused by the test drug itself (see Table 9B).

Such time-extended drop in arterial pressure observed herein, contributes substantially to the reduction of vascular resistance thereby alleviating the conditions associated with congestive heart failure over a longer period of time.

TABLE 9A

Response from Oral Administration of Compound 9
(Mean Arterial Pressure, mm Hg)

| | | Compound 9 (30 mg/kg) | |
| --- | --- | --- | --- |
| Time (min) | Ethanol/Vehicle | Fed | Starved |
| 0 | 139 ± 4 | 135 ± 7 | 133 ± 4 |
| 1 | 132 ± 4 | 132 ± 8 | 134 ± 6 |
| 5 | 127 ± 7 | 121 ± 7 | 129 ± 6 |
| 10 | 130 ± 6 | 120 ± 8 | 125 ± 6 |
| 15 | 131 ± 5 | 116 ± 10 | 122 ± 5 |
| 30 | 133 ± 8 | 109 ± 11 | 117 ± 5 |
| 45 | 131 ± 7 | 109 ± 11 | 114 ± 6 |
| 60 | 131 ± 8 | 112 ± 8 | 113 ± 6 |
| 90 | 123 ± 5 | 114 ± 8 | 111 ± 8 |
| 120 | 124 ± 9 | 107 ± 9 | 103 ± 9 |
| 150 | 127 ± 9 | 105 ± 10 | 109 ± 5 |
| 180 | 120 ± 12 | 107 ± 8 | 111 ± 5 |
| 210 | 127 ± 8 | 107 ± 8 | 114 ± 8 |
| 240 | 122 ± 8 | 106 ± 9 | 108 ± 8 |
| 270 | 120 ± 7 | 104 ± 12 | 104 ± 7 |
| 300 | 123 ± 2 | 104 ± 9 | 101 ± 9 |
| 330 | 120 ± 5 | 104 ± 9 | 102 ± 9 |
| 360 | 119 ± 6 | 104 ± 8 | 102 ± 10 |
| $A_{max}$ Time | $20 \pm 7^{360}$ | $33 \pm 9^{360}$ | $31 \pm 9^{360}$ |
| t½ | — | — | — |
| n | 5 | 5 | 5 |

TABLE 9B

Response from Oral Administration of Compound 9
(Heart Rate)

| | | Compound 9 (30 mg/kg) | |
| --- | --- | --- | --- |
| Time (min) | Ethanol Vehicle | Fed | Starved |
| 0 | 389 ± 15 | 384 ± 20 | 383 ± 10 |
| 1 | 375 ± 20 | 375 ± 21 | 381 ± 10 |
| 5 | 369 ± 17 | 377 ± 19 | 376 ± 10 |
| 10 | 379 ± 15 | 388 ± 15 | 382 ± 9 |
| 15 | 368 ± 19 | 385 ± 19 | 378 ± 11 |
| 30 | 366 ± 20 | 364 ± 21 | 367 ± 14 |
| 45 | 388 ± 25 | 360 ± 21 | 379 ± 8 |
| 60 | 372 ± 24 | 365 ± 23 | 380 ± 11 |
| 90 | 348 ± 18 | 355 ± 21 | 378 ± 17 |
| 120 | 349 ± 27 | 343 ± 21 | 369 ± 20 |

TABLE 9B-continued

Response from Oral Administration of Compound 9
(Heart Rate)

| | | Compound 9 (30 mglkg) | |
| --- | --- | --- | --- |
| Time (min) | Ethanol Vehicle | Fed | Starved |
| 150 | 332 ± 19 | 342 ± 14 | 373 ± 20 |
| 180 | 321 ± 13 | 361 ± 19 | 368 ± 19 |
| 210 | 337 ± 25 | 353 ± 19 | 374 ± 15 |
| 240 | 318 ± 11 | 353 ± 18 | 366 ± 19 |
| 270 | 307 ± 15 | 305 ± 27 | 343 ± 28 |
| 300 | 321 ± 20 | 316 ± 20 | 349 ± 24 |
| 330 | 303 ± 18 | 341 ± 19 | 356 ± 27 |
| 360 | 314 ± 17 | 343 ± 18 | 355 ± 32 |
| n | 5 | 5 | 5 |

Conclusion

These findings in the rat following intravenous administration of Compound 9 indicated that this molecule has a rapid onset of action with a long duration of action. However, despite having a ten-fold lower molecular weight, the potency of the Compound 9 as a vasodepressor was only comparable to that of the mPEG 5 kDa-amide Compound X (Compound 1) reported in a previous study. The reason for this is not readily apparent, but may reflect slower transformation to the active species. Such a possibility would be difficult to explain with the current knowledge of PEG derivatives, but may represent an important feature of the enzymatic hydrolysis of the amide linkage, as well as the removal of the protective acetyl moieties as the hydroxyl group. The lower molecular weight PEG may be less constrained than the more rigid higher molecular size PEG group, and may not allow adequate exposure of the amide linkage on the Compound X, making the molecule less amenable to attack and release of active species. How the different size substituents would affect the electrostatic charge distribution on Compound X benzindene chemical backbone is not known, but this could also modulate the rate of hydrolysis of the PEG analogue or the subsequently released free native Compound X, if this is the active species that elicits the hypotensive responses.

Previous studies with intravenous administration of the di-acetylated compounds linked to with 5,000 daltons or 20,000 daltons PEG through an amide bond showed that acetylation caused the molecules to produce a smaller, gradual fall in MAP with a slow rate of recovery. This gradual decline in MAP was not associated with reflex tachycardia. In contrast, in the present study, the Compound 9 had a rapid onset of action, and was associated with an initial fall in heart rate. Thus, it would appear that the protection of the hydroxyl groups by acetylation as in 5,000 or 20,000 daltons molecular weight PEG linked by ester or amide groups, does not modulate the release of the active species in the lower molecular weight compound. Whether this will also apply to the low molecular weight acetylated ester derivative will await further studies. However, it is of relevance that the acetylated form of the Compound X, not linked to PEG, likewise gave a rapid onset of action. This suggests that this chemical approach for attenuating the rapid onset of action following parenteral administration only operates in PEG derivatives of above 350 daltons.

Following oral administration, the highest doses of Compound 9 did produce a gradual fall in MAP, although the magnitude of this effect was obscured by the small gradual fall in MAP with the vehicle, that contained ethanol, the solvent required for solubilising the oil supplied. Because of the magnitude of this action lower doses were not investigated. However, this vasodepressor action was compared in both fasted and fed rats, the data suggests that there was comparable bioavailability under both these conditions. Because of the dissimilar nature of the blood pressure profile of Compound 9 following intravenous and oral administration, it is difficult to determine the absolute bioavailability by the oral route in these studies.

Previous findings that the hemodynamic profile of the acetylated mPEG 5,000 or 20,000 daltons Compound X amide derivatives was similar following intravenous or subcutaneous administration suggests slow activation, followed by slow metabolism or elimination of these analogs. By contrast, the current study with Compound 9 suggests that this compound does not offer an increased potency despite its lower molecular weight, nor the potential benefits of the slow onset of action of the cardiovascular events following parenteral administration. However, the use of the low molecular weight PEG derivatives may offer a rational chemical approach for the development of novel, long acting orally absorbed prostacyclin derivatives.

EXAMPLE 15

Evaluation of the Effects of mPEG 350 Da-ester-Compound X Diacetate on Systemic Hemodynamics in Anesthetized Rats In Vivo In this study, the cardiovascular activity of novel, lower polyethylene glycol (PEG) derivatives of the chemically stable benzindene analog of prostacyclin, Compound X, following intravenous administration in rats, is evaluated. The mPEG 350 Da -ester-Compound X Diacetate, hereinafter referred to as "Compound 10", was synthesized in an attempt to investigate the compound's effects on systemic hemodynamics.

Compound Under Evaluation

The compound tested was the acetylated mPEG 350 Da-ester-Compound X, hereinafter referred to as "Compound 10", in which the mPEG of 350 daltons molecular weight is linked to the carboxylic group of Compound X through an ester linkage and the hydroxyl groups of Compound X are acetylated.

Methods

Male Wistar rats (250–330 g) were anesthetized with thiopentone sodium (INTRAVAL®, 120 mg kg$^{-1}$ i.p.). The trachea was cannulated to facilitate respiration. The right carotid artery was cannulated and connected to a pressure transducer (Spectramed P23XL), for the measurement of mean arterial pressure (MAP) and heart rate (HR) which were continuously recorded on a 4-channel Grass 7D polygraph recorder (Grass, Mass., U.S.A.). The left femoral vein or the right jugular vein was cannulated for the administration of drugs. Body temperature was maintained at 37±1° C. by means of a rectal probe thermometer attached to a homeothermic blanket control unit (Harvard Apparatus Ltd.).

After a 15 minute stabilization period, Compound 10 (0.3, 3, 10 and 30 mg/kg) was administered as an intravenous bolus.

Compound 10 was dissolved in ethanol for storage at −20° C. Aliquots of the stock solution were removed for dilution in the aqueous vehicle prior to use.

Results

Intravenous administration of Compound 10 (0.3, 3, 10 and 30 mg/kg i.v.) caused a dose-related fall in MAP. (See Table 10A). Higher doses of Compound (10 and 30 mg/kg) caused a small increase in heart rate or reflex tachycardia, which was maximal at 45 minutes after administration of Compound 10. (See Table 10B).

TABLE 10A

Dose Response from Intravenous Administration of Compound 10 (Mean Arterial Pressure, mm Hg)

| | Compound 10 | | | |
|---|---|---|---|---|
| Time (min) | 0.3 mg/kg | 3 mg/kg | 10 mg/kg | 30 mg/kg |
| 0 | 110 ± 8 | 135 ± 6 | 122 ± 4 | 142 ± 7 |
| 1 | 104 ± 7 | 113 ± 6 | 94 ± 4 | 117 ± 2 |
| 5 | 105 ± 7 | 101 ± 9 | 88 ± 6 | 108 ± 9 |
| 10 | 106 ± 7 | 106 ± 7 | 87 ± 4 | 111 ± 7 |
| 15 | 103 ± 7 | 108 ± 5 | 86 ± 3 | 112 ± 8 |
| 30 | 106 ± 7 | 102 ± 4 | 87 ± 5 | 111 ± 8 |
| 45 | 105 ± 7 | 111 ± 5 | 92 ± 5 | 104 ± 3 |
| 60 | 103 ± 7 | 104 ± 2 | 92 ± 7 | 107 ± 3 |
| 75 | 108 ± 8 | 110 ± 4 | 91 ± 5 | 108 ± 4 |
| 90 | 102 ± 8 | 109 ± 3 | 89 ± 6 | 107 ± 4 |
| 105 | 100 ± 8 | 106 ± 2 | 91 ± 4 | 108 ± 4 |
| 120 | 108 ± 10 | 108 ± 3 | 92 ± 3 | 112 ± 8 |
| 135 | 111 ± 9 | 106 ± 2 | 90 ± 3 | 110 ± 6 |
| 150 | 108 ± 8 | 106 ± 7 | 91 ± 5 | 112 ± 8 |
| 165 | 106 ± 7 | 104 ± 4 | 91 ± 4 | 110 ± 6 |
| 180 | 104 ± 8 | 104 ± 2 | 89 ± 2 | 111 ± 8 |
| $\Delta_{max}^{Time}$ | 10 ± 4$^{105}$ | 33 ± 5$^{30}$ | 36 ± 4$^{15}$ | 41 ± 10$^{5}$ |
| $t_{½}$ | 15 | — | — | — |
| n | 5 | 5 | 5 | 5 |

TABLE 10B

Dose Response from Intravenous Administration of Compound 10 (Heart Rate)

| | Compound 10 | | | |
|---|---|---|---|---|
| Time (min) | 0.3 mg/kg | 3 mg/kg | 10 mg/kg | 30 mg/kg |
| 0 | 408 ± 15 | 428 ± 20 | 387 ± 14 | 384 ± 10 |
| 1 | 420 ± 13 | 438 ± 18 | 396 ± 12 | 396 ± 10 |
| 5 | 421 ± 16 | 420 ± 25 | 408 ± 15 | 400 ± 7 |
| 10 | 421 ± 16 | 420 ± 25 | 417 ± 14 | 414 ± 14 |
| 15 | 425 ± 17 | 426 ± 24 | 423 ± 15 | 414 ± 18 |
| 30 | 423 ± 15 | 435 ± 22 | 426 ± 18 | 429 ± 19 |
| 45 | 441 ± 17 | 447 ± 17 | 441 ± 16 | 423 ± 17 |
| 60 | 420 ± 16 | 444 ± 15 | 429 ± 13 | 420 ± 13 |
| 75 | 420 ± 20 | 444 ± 11 | 429 ± 13 | 414 ± 10 |
| 90 | 423 ± 19 | 441 ± 9 | 418 ± 8 | 417 ± 19 |
| 105 | 429 ± 17 | 423 ± 10 | 417 ± 10 | 407 ± 13 |
| 120 | 426 ± 22 | 426 ± 12 | 411 ± 8 | 408 ± 12 |
| 135 | 426 ± 22 | 421 ± 8 | 402 ± 6 | 399 ± 15 |
| 150 | 432 ± 27 | 429 ± 9 | 402 ± 9 | 400 ± 14 |
| 165 | 423 ± 26 | 426 ± 11 | 393 ± 9 | 402 ± 12 |
| 180 | 415 ± 32 | 429 ± 9 | 393 ± 11 | 393 ± 14 |
| $\Delta_{max}^{Time}$ | 33 ± 11$^{45}$ | 19 ± 7$^{45}$ | 54 ± 10$^{45}$ | 45 ± 20$^{30}$ |
| $t_{½}$ | ~45 | 75 | 75 | ~90 |
| n | 5 | 5 | 5 | 5 |

The systemic hemodynamic effects of Compound 10 were compared to the effects elicited by Compound 9 in Example 12.

At doses of 3 mg/kg, the fall in MAP caused by the Compound 10 was more pronounced (about 30 mm Hg) than that caused by the Compound 9 (maximum: about 15 mm Hg). The effects of both compounds on heart rate were similar.

At doses of 10 mg/kg, the fall in MAP caused by the Compound 10 was more pronounced (about 33 mm Hg) than that caused by the Compound 9 (maximum: about 25 mm Hg). The Compound 10 caused a small increase in heart rate, while the Compound 9 appeared to cause a small reduction in heart rate. The reduction in heart rate effect observed with Compound 9 may be due to the final concentration of ethanol in the vehicle of the Compound 9 (4.5% v/v) being greater than the final concentration of ethanol used as vehicle for the Compound 10 (2.5% v/v).

At 30 mg/kg, the maximum fall in MAP caused by the Compound 10 and Compound 9 were similar (about 45 mm Hg). The Compound 10 caused a small increase in heart rate, while the Compound 10 appeared to cause a small reduction in heart rate. The latter effect again may be due to the difference in concentration of ethanol in the vehicle of the Compound 9 (15% v/v) and the vehicle of Compound 10 (8.5% v/v).

The systemic hemodynamic effects of Compound 10 were also compared to those elicited by either mPEG 5 kDa-ester-Compound X diacetate (Compound 2) or mPEG 20 kDa-ester-Compound X diacetate (Compound 5). Clearly, according to the results, the fall in MAP was dependent on the size of the PEG-moiety, with compound possessing the lowest PEG molecular weight eliciting the largest fall in MAP. For instance, at 10 mg/kg, the maximum fall in MAP elicited by Compound 10 was 35 mm Hg, while the fall in MAP caused by Compound 5 was 20 mm Hg. Similarly the compound containing the lowest molecular weight PEG also caused the largest reflex tachycardia.

At 30 mg/kg, the maximum fall in MAP elicited by Compound 10 was about 40 mm Hg, while the fall in MAP caused by Compound 5 was about 30 mm Hg. The effects of all the compounds on heart rate were similar.

The systemic hemodynamic effects of Compound 9 were also compared to those elicited by either mPEG 5 kDa-amide-Compound X diacetate (Compound 8) or mPEG 20 kDa-amide-Compound X diacetate (Compound 7).

The fall in MAP was dependent on the size of the PEG-moiety, as the compound containing the lowest molecular weight PEG elicited the most rapid fall in MAP. For example, at 10 mg/kg, the fall in MAP elicited by Compound 9 within 1 minute was about 20 mm Hg (maximum: about 25 mm Hg at 60 minutes), while the fall in MAP caused by Compound 7 within 1 minute was negligible (maximum: about 30 mm Hg at 180 minutes). The Compound 9 which was dissolved in ethanol (4.5%) caused a small fall in heart rate, while the others (dissolved in acetate buffer) had not effect on heart rate.

At 30 mg/kg, the fall in MAP elicited by Compound 9 within 1 minute was about 45 mm Hg (maximum: about 45 mm Hg at 1 minute), while the fall in MAP caused by Compound 7 within one minute was negligible (maximum: about 30 mm Hg at 180 minutes). The Compound 9, which was dissolved in ethanol (15%) caused a significant fall in heart rate, while the others (dissolved in acetate buffer) had no effect on heart rate.

EXAMPLE 16

Effects of Compound X and PEG conjugated Compound X on Pulmonary Vascular Hypertension in Sheep In Vivo Each sheep was monitored for measurement of pulmonary arterial pressure (PPA), left atrial pressure (PLA), systemic arterial pressure (PSA), cardiac output (CO), and heart rate (HR). Plasma samples were taken from the sheep subjects to measure drug levels within the blood throughout the experiment. The experiment began upon intravenously infusing a known pulmonary arterial hypertension inducer in a customary manner. The rate of inducement was adjusted to cause the pulmonary vascular resistance (PVR) to increase 3 to 4 times that of the initial baseline PVR. PVR is calculated as the difference between PPA and PLA, divided by the CO. After a stabilization period, a sample of a present prostaglandin compound was administered via a surgically prepared tracheotomy using a MEDICATOR® aerosol drug delivery system (Healthline Medical Inc., Baldwin Park, Calif.), or via intravenous infusion.

Experiments were conducted to determine the effects of intravenously infused mPEG20 kDa-amide-compound X which was prepared similarly to Compound 1 of Example 1, and mPEG20 kDa-ester-compound X previously referred to as Compound 3 of Example 3, and aerosolized mPEG 20 kDa-ester-compound X (Compound 3) during pulmonary hypertension inducement. Referring to FIG. 1, after about a 15 minute baseline was established, pulmonary hypertension was induced by the intravenous administration of a known drug (a $PGH_2$ analog, U44069 or 9,11-dideoxy,9α, 11α-epoxymethanoprostaglandin $F_{2\alpha}$) into the sheep. After allowing the sheep to achieve a steady state for about 85 minutes, mPEG20 kDa-amide-Compound X (1.25 g I.V.) was intravenously infused into the sheep. After about 75 minutes of infusion of mPEG20 kDa-amide-Compound X, a complete reversal of the pulmonary arterial hypertension was observed for the rest of the duration of the experiment.

Figure 2:
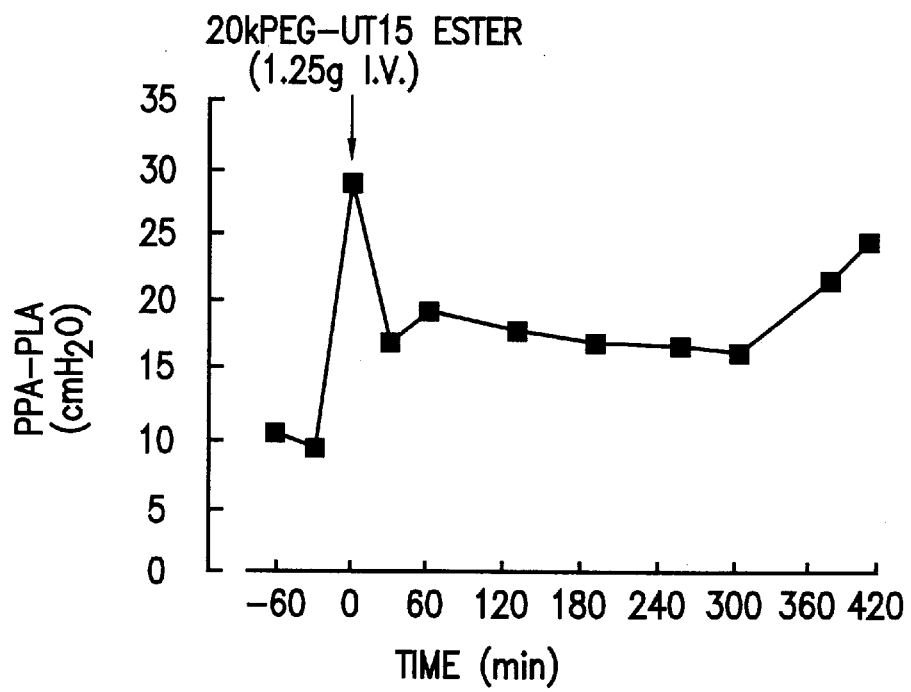
FIG. 2 is a graph depicting the effects of a dose of mPEG20 kDa-ester-Compound X, given as an intravenous bolus, on the pulmonary arterial pressure of a sheep intravenously-induced with a pulmonary hypertensive agent.

Referring to FIG. 2, a intravenous bolus administration of mPEG20 kDa-ester-Compound X (1.25 g I.V.) was made upon allowing the sheep to achieve a steady state for 30 minutes. The PPA-PLA reading dropped from about 28 $cmH_2O$ to about 17 $cmH_2O$ within 30 minutes after administration. The pressure remained depressed at about the same level for about 5 hours thereafter, and gradually rose to about 25 $cmH_2O$ over the next hour thereafter.

Referring to FIG. 3, after the sheep was permitted to achieve steady state for about 30 minutes after infusion of U44069, mPEG20 kDa-ester-Compound X (0.625 g) was administered as an aerosol for about 1 hour. The PPA-PLA rapidly dropped from about 32.5 $cmH_2O$ to about 21 $cmH_2O$. The pressure rose slightly to about 22.5 $cmH_2O$ before the aerosol infusion was discontinued. The pressure remained stable at about 22.5 $cmH_2O$ for about another 135 minutes and very gradually rose to about 32.5 $cmH_2O$ over 105 minutes thereafter.

Figure 4:
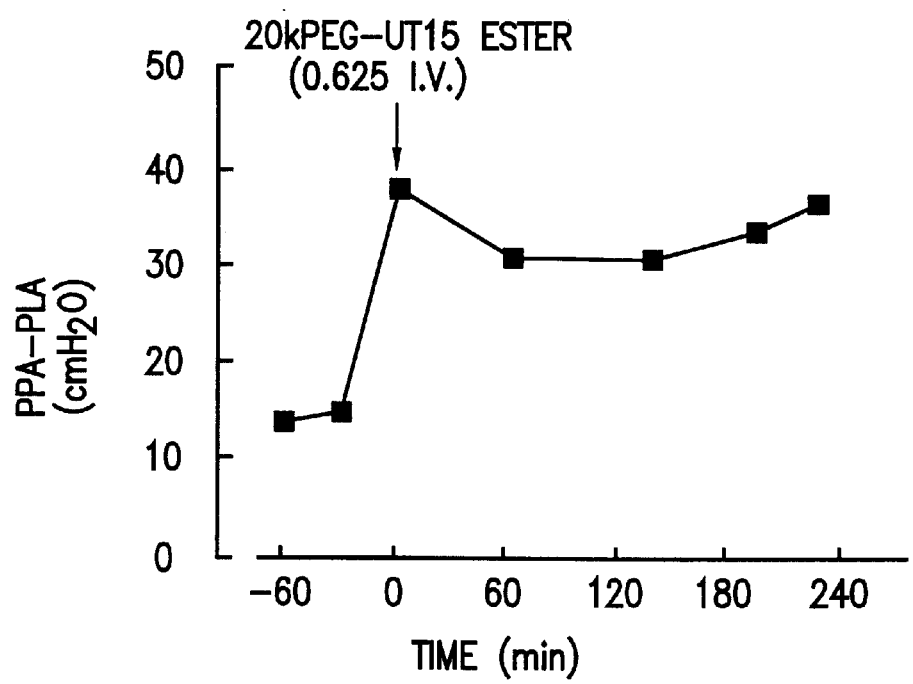
FIG. 4 is a graph depicting the effects of a dose of mPEG20 kDa-ester-Compound X, given as an intravenous bolus, on the pulmonary arterial pressure of a sheep intravenously-induced with a pulmonary hypertensive agent.

Referring to FIG. 4, the sheep was permitted to reach steady state for about 30 minutes after infusion of U44069, before a smaller intravenous bolus of mPEG 20 kDa-ester-Compound X (0.625 g I.V.) was administered. The PPA-PLA dropped to about 31 $cmH_2O$ from a maximum reading of about 37.5 over a 1 hour period. The pressure remained stable for about 90 minutes before the pressure began to slowly rise to about 35 $cmH_2O$ for about another hour thereafter.

Figure 5:
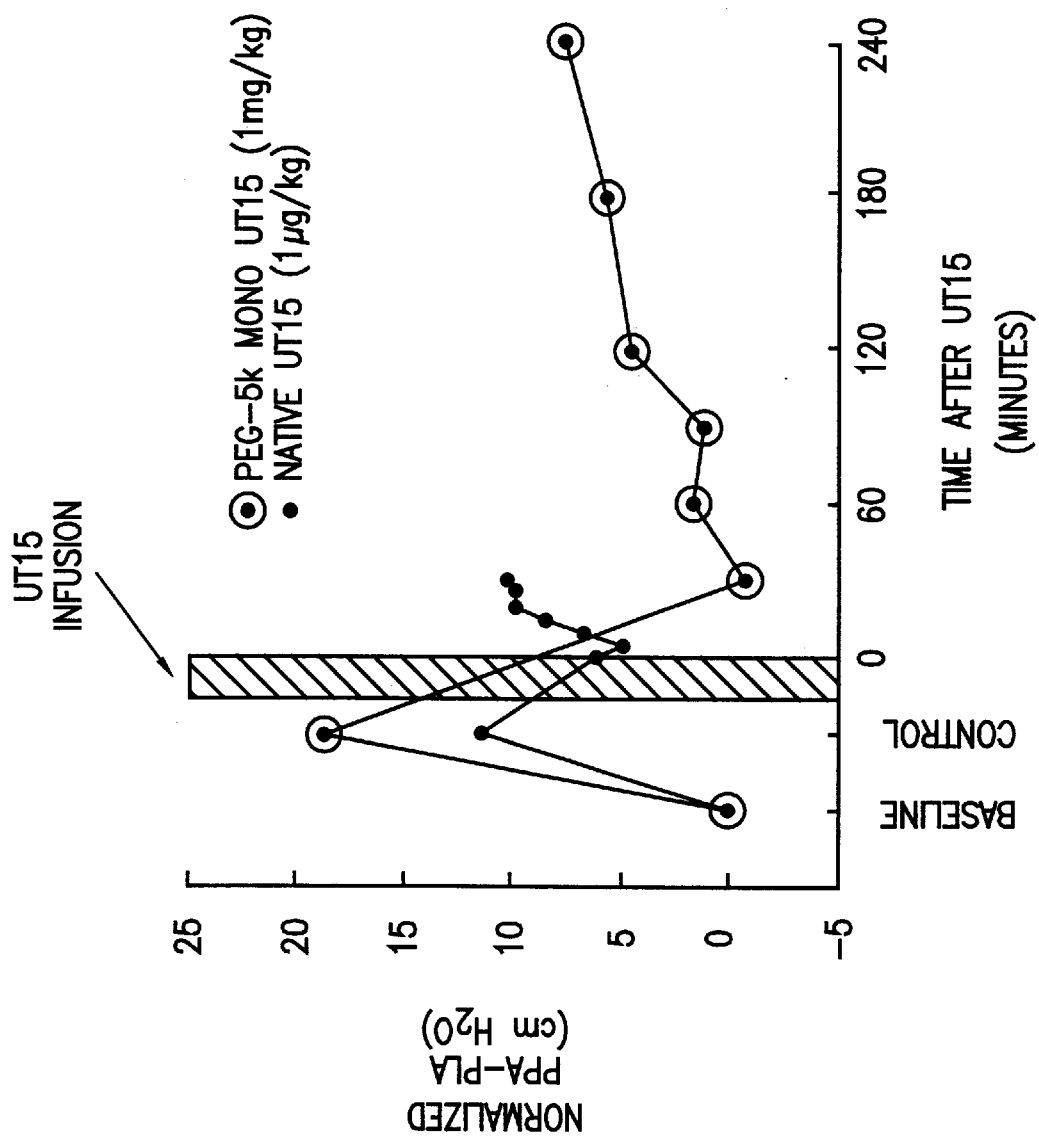
FIG. 5 is a graph showing the effects of mPEG5 kDa-ester-Compound X and native Compound X, each administered in the form of an aerosol on the pulmonary arterial pressure of respective sheep intravenously-induced with a pulmonary hypertensive agent.

Referring to FIG. 5, in another experiment, using the same methods described above, a comparison is shown between the effects of native Compound X and a mPEG5 k-ester-Compound X prepared similarly to Compound 3 of Example 3, during U44069-induced pulmonary hypertension. After allowing the U44069-infused sheep to reach steady state for about 90 minutes, native Compound X at 1 μg/kg was administered in an aerosol formulation over a 15 minute period. The PPA-PLA levels were normalized in this figure. A drop from about 11.25 $cmH_2O$ to about 5 $cmH_2O$ was observed 10 minutes after termination of the aerosolized infusion of native Compound X. Thereafter the pressure increased sharply to about $cmH_2O$ after only 30 minutes after termination of the Compound X infusion.

After allowing the U44069-infused sheep to reach steady state for about 90 minutes, mPEG5 k-ester-Compound X at 1 mg/kg was administered as an aerosol formulation over a 15 minute period. A substantial, dramatic drop in pressure from about 18.25 $cmH_2O$ to about 1 $cmH_2O$ below baseline reading occurred 30 minutes after the infusion was terminated. The pressure remained depressed at about 1.5 $cmH_2O$ for another hour thereafter. The pressure increased very gradually over the next 2.5 hours thereafter to about 7.5 $cmH_2O$. The pressure stayed below the 50% maximal reading over the entire 240 minute period after termination of the aerosolized infusion of mPEG5 k-ester-Compound X.

EXAMPLE 17

Systemic Hemodynamic Effects from Aerosolized Administration of Present Prostaglandin Compounds in Sheep in Vivo General Protocol The aerosolized administration of the present prostaglandin compounds to sheep subjects is performed to determine the effects of such compounds on systemic hemodynamics.

Each sheep is monitored for measurement of pulmonary arterial pressure (PPA), left atrial pressure (PLA), systemic arterial pressure (PSA), cardiac output (CO), and heart rate (HR). Plasma samples are taken from the sheep subjects to measure drug levels within the blood throughout the experiment. The experiment begins upon intravenously infusing U44069 (9,11-dideoxy,9α, 11α-epoxymethanoprostaglandin $F_{2\alpha}$, a $PGH_2$ analog) to artificially induce pulmonary arterial hypertension. The rate of U44069 infusion is adjusted to create pulmonary vascular resistance (PVR) to increase 3 to 4 times that of the initial baseline PVR. PVR is calculated as the difference between PPA and PLA, divided by the CO. After a stabilization period, one of the present prostaglandin compounds is administered via a surgically prepared tracheotomy using a MEDICATOR® aerosol drug delivery system (Healthline Medical Inc., Baldwin Park, Calif.).

Specific Protocols

A. A first series of experiments is performed to determine a reasonable effective dose of the present prostaglandin compounds which would reverse U44069-induced pulmonary arterial hypertension, and ascertain the effective period of the particular dose of present prostaglandin compounds administered.

After obtaining a baseline measurement of all listed variables for 20 minutes, U44069 is infused intravenously at a rate sufficient to cause PVR to increase 3 to 4 times its baseline value. After allowing 10 minutes to reach a relatively stable response, one of the present prostaglandin compounds, is administered via aerosol at a rate of 3000 ng per kg per minute for 60 minutes (i.e., for a 30 kg sheep: 3000 ng*30*60=5.4 mg of drug or 270 mg of drug/PEG). If the present prostaglandin compound provides a measurable effect on the elevated PVR, the U44069 is continuously infused until a stable response is observed. Upon reaching a stable response, the U44069 is discontinued for 20 minutes and resumed for another ten minutes. This process is repeated until the U44069 induced increase in PVR is no longer attenuated by the sample present prostaglandin compound.

If the sample compound dose is not effective from 30 to 60 minutes of its administration, the dosage is increased by a three-fold amount. If the sample compound dose is effective, then a new sheep subject is used and the experiment is repeated with the new dosage being one-third the previous dosage. This procedure is repeated until the minimal effective dosage and its corresponding effective dosage is determined.

B. A second series of experiments is performed to determine the effects of the present prostaglandin compounds on control sheep. Three doses of the present prostaglandin compounds is prepared for additional experiments. The first dose is the dose determined to be the minimal effective dose from the first series of experiments. The second dose of the present prostaglandin compounds is twice the minimal effective dose, and the third dose is five times that of the minimal effective dose. The sheep administered with the corresponding dose is monitored for a minimum of 2 hours per dose administered.

What is claimed:

1. A pharmaceutical composition for the treatment of congestive heart failure comprising a congestive heart failure treating effective amount of a compound of Formula Ia or Ib $$[P—T]_n—Z \qquad \text{Ia}$$

$$P—[T—Z]_n \qquad \text{Ib}$$

wherein P is a prostaglandin compound or analog thereof, T is an active group of P, and Z is a pharmaceutically acceptable group which is bound to T and which slows the metabolic rate of said compound;

n is an integer of at least 1, and pharmaceutically acceptable salts thereof; and a pharmaceutically acceptable carrier.

2. The pharmaceutical composition of claim 1 wherein T is selected from the group consisting a carboxyl group, a hydroxyl group, a carbonyl group, an oxidized carbohydrate, and a mercapto group.

3. The pharmaceutical composition of claim 1 wherein T is a carboxyl group or a hydroxyl group.

4. The pharmaceutical composition of claim 1 wherein Z is a pharmaceutically acceptable polymer or an acetyl group.

5. The pharmaceutical composition of claim 4 wherein the pharmaceutically acceptable polymers are selected from the group consisting of polyalkylene oxides, dextran, polyvinyl pyrrolidones, polyacrylamides, polyvinyl alcohols, and carbohydrate based polymers.

6. The pharmaceutical composition of claim 5 wherein the pharmaceutically acceptable polymers are selected from polyalkylene oxides.

7. The pharmaceutical composition of claim 6 wherein the polyalkylene oxides are selected from polyethylene glycols.

8. The pharmaceutical composition of claim 7 wherein the molecular weight of the polyethylene glycols is from about 200 to 80,000.

9. The pharmaceutical composition of claim 7 wherein the molecular weight of the polyethylene glycols is from about 2,000 to 42,000.

10. The pharmaceutical composition of claim 9 wherein the molecular weight of the polyethylene glycols is from about 5,000 to 25,000.

11. The pharmaceutical composition of claim 1 wherein said compound has the structure of Formula II

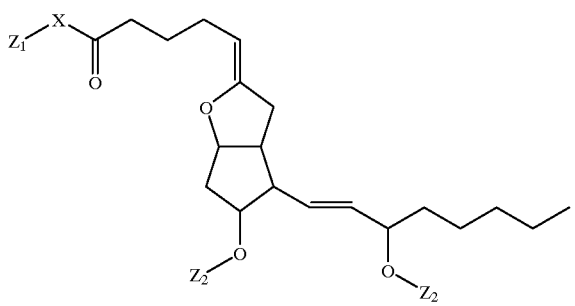

wherein $Z_1$ and $Z_2$ are each independently selected from the group consisting of hydrogen, a pharmaceutically acceptable polymer and an acetyl group with the proviso that at least one of $Z_1$ and $Z_2$ are not hydrogen, and X is selected from O and NH.

12. The pharmaceutical composition of claim 11 selected from Group 1 compounds wherein $Z_1$ is a pharmaceutically acceptable polymer, X is selected from O and NH and each $Z_2$ is independently selected from hydrogen and an acetyl group.

13. The pharmaceutical composition of claim 11 selected from Group 2 compounds wherein $Z_1$ is hydrogen, X is selected from O and at least one $Z_2$ is a pharmaceutically acceptable polymer attached to the oxygen atom through an ester group.

14. The pharmaceutical composition of claim 11 selected from Group 3 compounds wherein $Z_1$ is a pharmaceutically acceptable polymer, X is selected from O and NH and at least one $Z_2$ is a pharmaceutically acceptable polymer attached to the oxygen atom through an ester group.

15. The pharmaceutical composition of claim 1 wherein said compound has the structure of Formula III

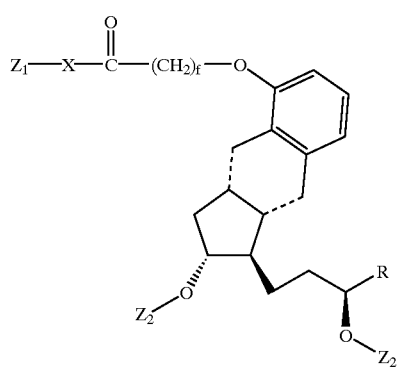

wherein
$Z_1$ and $Z_2$ are each independently selected from the group consisting of hydrogen, a pharmaceutically acceptable polymer and an acetyl group,
f is an integer of from 1 to 3;
X is selected from O and NH; and
R is selected from hydrogen and an alkyl group.

16. The pharmaceutical composition of claim 15 wherein R is an alkyl group having 1–6 carbon atoms.

17. The pharmaceutical composition of claim 15 selected from Group 4 compounds wherein $Z_1$ is a pharmaceutically acceptable polymer, X is selected from O and NH and each $Z_2$ is independently selected from hydrogen and an acetyl group.

18. The pharmaceutical composition of claim 15 selected from group 5 compounds wherein $Z_1$ is hydrogen, X is O and each $Z_2$ is an acetyl group or a pharmaceutically acceptable polymer attached to the oxygen atom through an ester or an ether group.

19. The pharmaceutical composition of claim 15 selected from Group 6 compounds wherein $Z_1$ is a pharmaceutically acceptable polymer, X is selected from O and NH and each $Z_2$ is a pharmaceutically acceptable polymer attached to the oxygen atom through an ester or an ether group.

20. The pharmaceutical composition of claim 11 where the pharmaceutically acceptable polymer is a polyethylene glycol having a molecular weight of from about 200 to 80,000.

21. The pharmaceutical composition of claim 20 wherein the molecular weight of the polyethylene glycol is from about 2,000 to 42,000.

22. The pharmaceutical composition of claim 15 where the pharmaceutically acceptable polymer is a polyethylene glycol having a molecular weight of from about 200 to 80,000.

23. The pharmaceutical composition of claim 22 wherein the molecular weight of the polyethylene glycol is from about 2,000 to 42,000.

24. The pharmaceutical composition of claim 15 wherein said compound has the structure of Formula IV

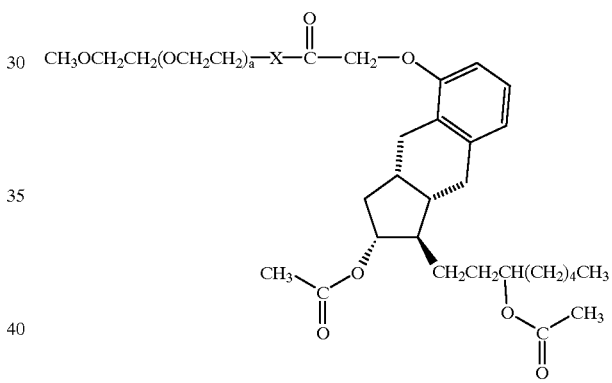

wherein a is from about 6 to 600.

25. The pharmaceutical composition of claim 15 wherein $Z_1$ is a methyl terminated polyethylene glycol having a molecular weight of about 5,000, X is NH and each $Z_2$ is hydrogen.

26. The pharmaceutical composition of claim 15 wherein $Z_1$ is a methyl terminated polyethylene glycol having a molecular weight of about 5,000, X is O and each $Z_2$ is an acetyl group.

27. The pharmaceutical composition of claim 15 wherein $Z_1$ is hydrogen and each $Z_2$ is a methyl terminated polyethylene glycol having a molecular weight of about 20,000 attached to the oxygen atom through a group —O—$(CH_2)_2$—CO—.

28. The pharmaceutical composition of claim 15 wherein $Z_1$ is hydrogen and each $Z_2$ is an acetyl group.

29. The pharmaceutical composition of claim 15 wherein $Z_1$ is a methyl terminated polyethylene glycol having a molecular weight of about 20,000, X is O, and each $Z_2$ is an acetyl group.

30. The pharmaceutical composition of claim 15 wherein $Z_1$ is a methyl terminated polyethylene glycol having a molecular weight of about 20,000, X is NH and each $Z_2$ is hydrogen.

31. The pharmaceutical composition of claim 15 wherein $Z_1$ is a methyl terminated polyethylene glycol having a molecular weight of about 20,000, X is NH and each $Z_2$ is an acetyl group.

32. The pharmaceutical composition of claim 15 wherein $Z_1$ is a methyl terminated polyethylene glycol having a molecular weight of about 5,000, X is NH and each $Z_2$ is an acetyl group.

33. The pharmaceutical composition of claim 15 wherein $Z_1$ is a methyl terminated polyethylene glycol having a molecular weight of about 350, X is NH and each $Z_2$ is an acetyl group.

34. The pharmaceutical composition of claim 15 wherein $Z_1$ is a methyl terminated polyethylene glycol having a molecular weight of about 350, X is O and each $Z_2$ is an acetyl group.

35. The pharmaceutical composition of claim 1, wherein P is a PGE-type prostaglandin.

36. A method of treating congestive heart failure comprising administering to a warm-blooded animal the pharmaceutical composition of claim 1.

37. The method of claim 35 comprising administering said pharmaceutical composition in an amount sufficient to provide from about 0.5 to 100 mg/kg/day to said warm-blooded animal.

38. The method of claim 35 wherein T is selected from the group consisting a carboxyl group, a hydroxyl group, a carbonyl group, an oxidized carbohydrate, and a mercapto group.

39. The method of claim 35 wherein T is a carboxyl group or a hydroxyl group.

40. The method of claim 35 wherein Z is a pharmaceutically acceptable polymer or an acetyl group.

41. The method of claim 39 wherein the pharmaceutically acceptable polymers are selected from the group consisting of polyalkylene oxides, dextran, polyvinyl pyrrolidones, polyacrylamides, polyvinyl alcohols, and carbohydrate based polymers.

42. The method of claim 40 wherein the pharmaceutically acceptable polymers are selected from polyalkylene oxides.

43. The method of claim 41 wherein the polyalkylene oxides are selected from polyethylene glycols.

44. The method of claim 42 wherein the molecular weight of the polyethylene glycols is from 200 to 80,000.

45. The method of claim 42 wherein the molecular weight of the polyethylene glycols is from 2,000 to 42,000.

46. The method of claim 45 wherein the molecular weight of the polyethylene glycols is from about 5,000 to 25,000.

47. The method of claim 35 comprising administering said pharmaceutical composition intravenously to said warm-blooded animal.

48. The method of claim 35 comprising administering said pharmaceutical composition subcutaneously to said warm-blooded animal.

49. The method of claim 35 comprising administering said pharmaceutical composition by inhalation to said warm-blooded animal.

50. The method of claim 35 comprising administering said pharmaceutical composition orally to said warm-blooded animal.

51. The method of claim 35, wherein P is a PGE-type prostaglandin.

* * * * *

UNITED STATES PATENT AND TRADEMARK OFFICE
CERTIFICATE OF CORRECTION

PATENT NO. : 6,242,482 B1
DATED : June 5, 2001
INVENTOR(S) : Robert Shorr et al.

It is certified that error appears in the above-identified patent and that said Letters Patent is hereby corrected as shown below:

<u>Column 41,</u>
Line 22, change "35" to -- 36 --;
Line 26, change "35" to -- 36 --;
Line 32, change "35" to -- 36 --;

<u>Column 42,</u>
Line 17, change "35" to -- 36 --;
Line 20, change "35" to -- 36 --;
Line 23, change "35" to -- 36 --;
Line 26, change "35" to -- 36 --; and
Line 30, change "35" to -- 36 --;

Signed and Sealed this

Sixteenth Day of July, 2002

*Attest:*

*Attesting Officer*

JAMES E. ROGAN
*Director of the United States Patent and Trademark Office*